United States Patent [19]

Kim et al.

[11] Patent Number: 5,552,520
[45] Date of Patent: Sep. 3, 1996

[54] THERAPEUTIC PEPTIDE DERIVATIVES

[75] Inventors: Sun H. Kim, Chestnut Hill; Susan R. Keyes, Boston; Sylviane Moreau, Upton; Zheng X. Dong, Framingham; John Taylor, Upton, all of Mass.

[73] Assignee: Biomeasure, Inc., Milford, Mass.

[21] Appl. No.: 287,957

[22] Filed: Aug. 9, 1994

Related U.S. Application Data

[63] Continuation-in-part of Ser. No. 104,194, Aug. 9, 1993, abandoned.

[51] Int. Cl.$^6$ .............................. C07K 5/00; C07K 7/00; C07K 17/00
[52] U.S. Cl. .................. 530/311; 530/326; 530/327; 530/328; 530/329; 530/306; 530/307; 530/308; 530/309; 530/312; 530/313; 530/314
[58] Field of Search ...................................... 530/311, 324, 530/326–329, 306–309, 312–314; 514/12–16

[56] References Cited

U.S. PATENT DOCUMENTS 4,837,303   6/1989   Jung ........................................ 530/311

FOREIGN PATENT DOCUMENTS

WO88/02756   4/1988   WIPO .
WO89/09786   10/1989   WIPO .

*Primary Examiner*—Toni R. Scheiner
*Assistant Examiner*—Sheela J. Huff
*Attorney, Agent, or Firm*—Fish & Richardson P.C.; William E. McGowan

[57] ABSTRACT

Peptide derivatives containing one or more substituents separately linked by an amide, amino or sulfonamide bond to an amino group on either the N-terminal end or side chain of a biologically active peptide moiety. The peptide derivatives have relatively enhanced biological activity when compared to the corresponding peptide alone.

28 Claims, 1 Drawing Sheet

SEQUENCE LISTING ( 1 ) GENERAL INFORMATION:

( i i i ) NUMBER OF SEQUENCES: 116

( 2 ) INFORMATION FOR SEQ ID NO: 1:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is
            D- Tryptophan;
            Xaa at position 5 is 2-Amino-
            butyric acid ( x i ) SEQUENCE DESCRIPTION: SEQ ID NO: 1:

Cys Tyr Xaa Lys Xaa Cys
1           5

( 2 ) INFORMATION FOR SEQ ID NO: 2:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-
            Tryptophan ( x i ) SEQUENCE DESCRIPTION: SEQ ID NO: 2:

Cys Tyr Xaa Lys Thr Cys
1           5

( 2 ) INFORMATION FOR SEQ ID NO: 3:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-Tryptophan ( x i ) SEQUENCE DESCRIPTION: SEQ ID NO: 3:

Cys Tyr Xaa Lys Val Cys
1                     5

( 2 ) INFORMATION FOR SEQ ID NO: 4:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-beta-Napthalalanine;
                    Xaa at position 4 is D-Tryptophan ( x i ) SEQUENCE DESCRIPTION: SEQ ID NO: 4:

Xaa Cys Tyr Xaa Lys Thr Cys Thr
1                     5

( 2 ) INFORMATION FOR SEQ ID NO: 5:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-Phenylalanine;
                    Xaa at position 4 is D-Tryptophan;
                    Xaa at position 8 is beta-Napthalalanine ( x i ) SEQUENCE DESCRIPTION: SEQ ID NO: 5:

Xaa Cys Phe Xaa Lys Thr Cys Xaa
1                     5

( 2 ) INFORMATION FOR SEQ ID NO: 6:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-Phenylalanine;
                    Xaa at position 4 is D-Tryptophan;
                    Xaa at position 8 is beta-Napthalalanine ( x i ) SEQUENCE DESCRIPTION: SEQ ID NO: 6:

Xaa Cys Tyr Xaa Lys Thr Cys Xaa
1                     5

( 2 ) INFORMATION FOR SEQ ID NO: 7:

( i ) SEQUENCE CHARACTERISTICS:
           ( A ) LENGTH: 8
           ( B ) TYPE: amino acid
           ( C ) STRANDEDNESS: single
           ( D ) TOPOLOGY: linear ( i x ) FEATURE:
           ( D ) OTHER INFORMATION: Xaa at position 1 is D-beta-
                Napthalalanine;
                Xaa at position 4 is D-
                Tryptophan ( x i ) SEQUENCE DESCRIPTION: SEQ ID NO: 7:

Xaa Cys Phe Xaa Lys Thr Cys Thr
 1               5

( 2 ) INFORMATION FOR SEQ ID NO: 8:

( i ) SEQUENCE CHARACTERISTICS:
           ( A ) LENGTH: 8
           ( B ) TYPE: amino acid
           ( C ) STRANDEDNESS: single
           ( D ) TOPOLOGY: linear ( i x ) FEATURE:
           ( D ) OTHER INFORMATION: Xaa at position 1 is D-
                Phenylalanine;
                Xaa at position 4 is D-
                Tryptophan;
                Xaa at position 7 is
                Penicillenine ( x i ) SEQUENCE DESCRIPTION: SEQ ID NO: 8:

Xaa Cys Tyr Xaa Lys Thr Xaa Thr
 1               5

( 2 ) INFORMATION FOR SEQ ID NO: 9:

( i ) SEQUENCE CHARACTERISTICS:
           ( A ) LENGTH: 8
           ( B ) TYPE: amino acid
           ( C ) STRANDEDNESS: single
           ( D ) TOPOLOGY: linear ( i x ) FEATURE:
           ( D ) OTHER INFORMATION: Xaa at position 1 is D-
                Phenylalanine;
                Xaa at position 4 is D-
                Tryptophan;
                Xaa at position 7 is
                Penicillenine ( x i ) SEQUENCE DESCRIPTION: SEQ ID NO: 9:

Xaa Cys Phe Xaa Lys Thr Xaa Thr
 1               5

( 2 ) INFORMATION FOR SEQ ID NO: 10:

( i ) SEQUENCE CHARACTERISTICS:
           ( A ) LENGTH: 8
           ( B ) TYPE: amino acid
           ( C ) STRANDEDNESS: single
           ( D ) TOPOLOGY: linear ( i x ) FEATURE:
           ( D ) OTHER INFORMATION: Xaa at position 2 is
                Penicillenine;
                Xaa at position 4 is D-
                Tryptophan ( x i ) SEQUENCE DESCRIPTION: SEQ ID NO: 10:

Gly Xaa Phe Xaa Lys Thr Cys Thr
 1               5

( 2 ) INFORMATION FOR SEQ ID NO: 11:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 2 is
            Penicillenine;
            Xaa at position 4 is D-
            Tryptophan ( x i ) SEQUENCE DESCRIPTION: SEQ ID NO: 11:

Phe Xaa Tyr Xaa Lys Thr Cys Thr
 1               5

( 2 ) INFORMATION FOR SEQ ID NO: 12:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at positions 2 and 7 are
            Penicillenine;
            Xaa at position 4 is D-
            Tryptophan ( x i ) SEQUENCE DESCRIPTION: SEQ ID NO: 12:

Phe Xaa Phe Xaa Lys Thr Xaa Thr
 1               5

( 2 ) INFORMATION FOR SEQ ID NO: 13:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-
            Phenylalanine;
            Xaa at position 4 is D-
            Tryptophan ( x i ) SEQUENCE DESCRIPTION: SEQ ID NO: 13:

Xaa Cys Phe Xaa Lys Thr Cys Thr
 1               5

( 2 ) INFORMATION FOR SEQ ID NO: 14:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at positions 1 and 4 are D-
            Tryptophan ( x i ) SEQUENCE DESCRIPTION: SEQ ID NO: 14:

Xaa Cys Tyr Xaa Lys Val Cys Thr
1               5

( 2 ) INFORMATION FOR SEQ ID NO: 15:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at positions 1 and 4 are D-
            Tryptophan ( x i ) SEQUENCE DESCRIPTION: SEQ ID NO: 15:

Xaa Cys Phe Xaa Lys Thr Cys Thr
1               5

( 2 ) INFORMATION FOR SEQ ID NO: 16:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-
            Phenylalanine;
            Xaa at position 4 is D-
            Tryptophan ( x i ) SEQUENCE DESCRIPTION: SEQ ID NO: 16:

Xaa Cys Tyr Xaa Lys Val Cys Thr
1               5

( 2 ) INFORMATION FOR SEQ ID NO: 17:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-
            Phenylalanine;
            Xaa at position 4 is D-
            Tryptophan ( x i ) SEQUENCE DESCRIPTION: SEQ ID NO: 17:

Xaa Cys Tyr Xaa Lys Val Cys Trp
1               5

( 2 ) INFORMATION FOR SEQ ID NO: 18:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-
            Phenylalanine;
            Xaa at position 4 is D-
            Tryptophan ( x i ) SEQUENCE DESCRIPTION: SEQ ID NO: 18:

Xaa Lys Tyr Xaa Lys Val Asp Thr
1               5

( 2 ) INFORMATION FOR SEQ ID NO: 19:

( i ) SEQUENCE CHARACTERISTICS:
        ( A ) LENGTH: 9
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is
        hArginine (Et)$_2$;
        Xaa at position 5 is D-
        Tryptophan ( x i ) SEQUENCE DESCRIPTION: SEQ ID NO: 19:

Xaa Gly Cys Phe Xaa Lys Thr Cys Thr
1                     5

( 2 ) INFORMATION FOR SEQ ID NO: 20:

( i ) SEQUENCE CHARACTERISTICS:
        ( A ) LENGTH: 9
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is
        D-hArginine (Et)$_2$;
        Xaa at position 5 is D-
        Tryptophan ( x i ) SEQUENCE DESCRIPTION: SEQ ID NO: 20:

Xaa Gly Cys Phe Xaa Lys Thr Cys Thr
1                     5

( 2 ) INFORMATION FOR SEQ ID NO: 21:

( i ) SEQUENCE CHARACTERISTICS:
        ( A ) LENGTH: 9
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-hArginine
        ( B u );
        Xaa at position 5 is D-
        Tryptophan ( x i ) SEQUENCE DESCRIPTION: SEQ ID NO: 21:

Xaa Gly Cys Phe Xaa Lys Thr Cys Thr
1                     5

( 2 ) INFORMATION FOR SEQ ID NO: 22:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-hArginine
        ( E t )$_2$;
        Xaa at position 4 is D-
        Tryptophan ( x i ) SEQUENCE DESCRIPTION: SEQ ID NO: 22:

Xaa Cys Phe Xaa Lys Thr Cys Thr
1                5

( 2 ) INFORMATION FOR SEQ ID NO: 23:

( i ) SEQUENCE CHARACTERISTICS:
      ( A ) LENGTH: 8
      ( B ) TYPE: amino acid
      ( C ) STRANDEDNESS: single
      ( D ) TOPOLOGY: linear ( i x ) FEATURE:
      ( D ) OTHER INFORMATION: Xaa at position 1 is L-hArginine
         $(Et)_2$;
         Xaa at position 4 is D-
         Tryptophan ( x i ) SEQUENCE DESCRIPTION: SEQ ID NO: 23:

Xaa Cys Phe Xaa Lys Thr Cys Thr
 1                    5

( 2 ) INFORMATION FOR SEQ ID NO: 24:

( i ) SEQUENCE CHARACTERISTICS:
      ( A ) LENGTH: 8
      ( B ) TYPE: amino acid
      ( C ) STRANDEDNESS: single
      ( D ) TOPOLOGY: linear ( i x ) FEATURE:
      ( D ) OTHER INFORMATION: Xaa at position 1 is D-hArginine
         $(CH_2CF_3)_2$;
         Xaa at position 4 is D-
         Tryptophan ( x i ) SEQUENCE DESCRIPTION: SEQ ID NO: 24:

Xaa Cys Phe Xaa Lys Thr Cys Thr
 1                    5

( 2 ) INFORMATION FOR SEQ ID NO: 25:

( i ) SEQUENCE CHARACTERISTICS:
      ( A ) LENGTH: 9
      ( B ) TYPE: amino acid
      ( C ) STRANDEDNESS: single
      ( D ) TOPOLOGY: linear ( i x ) FEATURE:
      ( D ) OTHER INFORMATION: Xaa at position 1 is D-hArginine
         $(CH_2CF_3)_2$;
         Xaa at position 5 is D-
         Tryptophan ( x i ) SEQUENCE DESCRIPTION: SEQ ID NO: 25:

Xaa Gly Cys Phe Xaa Lys Thr Cys Thr
 1                    5

( 2 ) INFORMATION FOR SEQ ID NO: 26:

( i ) SEQUENCE CHARACTERISTICS:
      ( A ) LENGTH: 9
      ( B ) TYPE: amino acid
      ( C ) STRANDEDNESS: single
      ( D ) TOPOLOGY: linear ( i x ) FEATURE:
      ( D ) OTHER INFORMATION: Xaa at position 1 is D-hArginine
         $(CH_2CF_3)_2$;
         Xaa at position 5 is D-
         Tryptophan ( x i ) SEQUENCE DESCRIPTION: SEQ ID NO: 26:

Xaa Gly Cys Phe Xaa Lys Thr Cys Phe
 1                    5

(2) INFORMATION FOR SEQ ID NO: 27:

(i) SEQUENCE CHARACTERISTICS:
       (A) LENGTH: 9
       (B) TYPE: amino acid
       (C) STRANDEDNESS: single
       (D) TOPOLOGY: linear (ix) FEATURE:
       (D) OTHER INFORMATION: Xaa at position 1 is L-hArginine
           $(CH_2CF_3)_2$;
           Xaa at position 5 is D-
           Tryptophan (xi) SEQUENCE DESCRIPTION: SEQ ID NO: 27:

Xaa Gly Cys Phe Xaa Lys Thr Cys Thr
 1                   5

(2) INFORMATION FOR SEQ ID NO: 28:

(i) SEQUENCE CHARACTERISTICS:
       (A) LENGTH: 9
       (B) TYPE: amino acid
       (C) STRANDEDNESS: single
       (D) TOPOLOGY: linear (ix) FEATURE:
       (D) OTHER INFORMATION: Xaa at position 1 is D-hArginine
           $(CH_2CF_3)_2$;
           Xaa at position 5 is D-
           Tryptophan;
           Xaa at position 6 is N-
           Methylvaline (xi) SEQUENCE DESCRIPTION: SEQ ID NO: 28:

Xaa Gly Cys Phe Xaa Xaa Thr Cys Thr
 1                   5

(2) INFORMATION FOR SEQ ID NO: 29:

(i) SEQUENCE CHARACTERISTICS:
       (A) LENGTH: 9
       (B) TYPE: amino acid
       (C) STRANDEDNESS: single
       (D) TOPOLOGY: linear (ix) FEATURE:
       (D) OTHER INFORMATION: Xaa at position 1 is hArginine
           $(CH_2, hexyl)$;
           Xaa at position 5 is D-
           Tryptophan (xi) SEQUENCE DESCRIPTION: SEQ ID NO: 29:

Xaa Gly Cys Phe Xaa Lys Thr Cys Thr
 1                   5

(2) INFORMATION FOR SEQ ID NO: 30:

(i) SEQUENCE CHARACTERISTICS:
       (A) LENGTH: 9
       (B) TYPE: amino acid
       (C) STRANDEDNESS: single
       (D) TOPOLOGY: linear (ix) FEATURE:
       (D) OTHER INFORMATION: Xaa at position 1 is hArginine
           $(hexyl_2)$;
           Xaa at position 5 is D-
           Tryptophan (xi) SEQUENCE DESCRIPTION: SEQ ID NO: 30:

Xaa Gly Cys Phe Xaa Lys Thr Cys Thr
1               5

( 2 ) INFORMATION FOR SEQ ID NO: 31:

( i ) SEQUENCE CHARACTERISTICS:
      ( A ) LENGTH: 9
      ( B ) TYPE: amino acid
      ( C ) STRANDEDNESS: single
      ( D ) TOPOLOGY: linear ( i x ) FEATURE:
      ( D ) OTHER INFORMATION: Xaa at position 1 is D-hArginine
         ( E t )$_2$;
         Xaa at position 5 is D-
         Tryptophan ( x i ) SEQUENCE DESCRIPTION: SEQ ID NO: 31:

Xaa Gly Cys Phe Xaa Lys Thr Cys Thr
1               5

( 2 ) INFORMATION FOR SEQ ID NO: 32:

( i ) SEQUENCE CHARACTERISTICS:
      ( A ) LENGTH: 9
      ( B ) TYPE: amino acid
      ( C ) STRANDEDNESS: single
      ( D ) TOPOLOGY: linear ( i x ) FEATURE:
      ( D ) OTHER INFORMATION: Xaa at position 1 is D-hArginine
         ( E t )$_2$;
         Xaa at position 5 is D-
         Tryptophan ( x i ) SEQUENCE DESCRIPTION: SEQ ID NO: 32:

Xaa Gly Cys Phe Xaa Lys Thr Cys Phe
1               5

( 2 ) INFORMATION FOR SEQ ID NO: 33:

( i ) SEQUENCE CHARACTERISTICS:
      ( A ) LENGTH: 9
      ( B ) TYPE: amino acid
      ( C ) STRANDEDNESS: single
      ( D ) TOPOLOGY: linear ( i x ) FEATURE:
      ( D ) OTHER INFORMATION: Xaa at position 1 is D-hArginine
         ( E t )$_2$;
         Xaa at position 5 is
         D- Tryptophan;
         Xaa at position 6 is
         Lysine- (iPr)

( x i ) SEQUENCE DESCRIPTION: SEQ ID NO: 33:

Xaa Gly Cys Phe Xaa Xaa Thr Cys Thr
1               5

( 2 ) INFORMATION FOR SEQ ID NO: 34:

( i ) SEQUENCE CHARACTERISTICS:
      ( A ) LENGTH: 10
      ( B ) TYPE: amino acid
      ( C ) STRANDEDNESS: single
      ( D ) TOPOLOGY: linear ( i x ) FEATURE:
      ( D ) OTHER INFORMATION: Xaa at position 1 is
         D-beta- Napthalalanine;
         Xaa at position 5 is D-
         Tryptophan;
         Xaa at position 10 is hArginine (Et)₂

(xi) SEQUENCE DESCRIPTION: SEQ ID NO: 34:

Xaa Gly Cys Phe Xaa Lys Thr Cys Gly Xaa
 1               5                   10

(2) INFORMATION FOR SEQ ID NO: 35:

(i) SEQUENCE CHARACTERISTICS:
        (A) LENGTH: 10
        (B) TYPE: amino acid
        (C) STRANDEDNESS: single
        (D) TOPOLOGY: linear (ix) FEATURE:
        (D) OTHER INFORMATION: Xaa at position 1 is D-Lysine
            (iPr);
            Xaa at position 5 is
            D-Tryptophan (xi) SEQUENCE DESCRIPTION: SEQ ID NO: 35:

Xaa Gly Cys Phe Xaa Lys Thr Cys Gly Arg
 1               5                   10

(2) INFORMATION FOR SEQ ID NO: 36:

(i) SEQUENCE CHARACTERISTICS:
        (A) LENGTH: 10
        (B) TYPE: amino acid
        (C) STRANDEDNESS: single
        (D) TOPOLOGY: linear (ix) FEATURE:
        (D) OTHER INFORMATION: Xaa at positions 1 and 2 are D-
            hArginine ($CH_2CF_3$)₂;
            Xaa at position 6 is D-
            Tryptophan (xi) SEQUENCE DESCRIPTION: SEQ ID NO: 36:

Xaa Xaa Gly Cys Phe Xaa Lys Thr Cys Thr
 1               5                   10

(2) INFORMATION FOR SEQ ID NO: 37:

(i) SEQUENCE CHARACTERISTICS:
        (A) LENGTH: 10
        (B) TYPE: amino acid
        (C) STRANDEDNESS: single
        (D) TOPOLOGY: linear (ix) FEATURE:
        (D) OTHER INFORMATION: Xaa at positions 1 and 2 are D-
            hArginine ($CH_2CF_3$)₂;
            Xaa at position 6 is D-
            Tryptophan (xi) SEQUENCE DESCRIPTION: SEQ ID NO: 37:

Xaa Xaa Gly Cys Phe Xaa Lys Thr Cys Phe
 1               5                   10

(2) INFORMATION FOR SEQ ID NO: 38:

(i) SEQUENCE CHARACTERISTICS:
        (A) LENGTH: 10
        (B) TYPE: amino acid
        (C) STRANDEDNESS: single
        (D) TOPOLOGY: linear (ix) FEATURE:
        (D) OTHER INFORMATION: Xaa at positions 1 and 2 are D-
            hArginine (Et)₂;
            Xaa at position 6 is D-

Tryptophan (xi) SEQUENCE DESCRIPTION: SEQ ID NO: 38:

Xaa Xaa Gly Cys Phe Xaa Lys Thr Cys Thr
 1               5                      10

(2) INFORMATION FOR SEQ ID NO: 39:

(i) SEQUENCE CHARACTERISTICS:
        (A) LENGTH: 12
        (B) TYPE: amino acid
        (C) STRANDEDNESS: single
        (D) TOPOLOGY: linear (ix) FEATURE:
        (D) OTHER INFORMATION: Xaa at position 4 is 4-Cl-Phenyalanine
            Xaa at position 6 is D-Tryptophan
            Xaa at position 12 is D- Cysteine (xi) SEQUENCE DESCRIPTION: SEQ ID NO: 39:

Cys Lys Asn Xaa Phe Xaa Lys Thr Phe Thr Ser Xaa
 1               5                      10

(2) INFORMATION FOR SEQ ID NO: 40:

(i) SEQUENCE CHARACTERISTICS:
        (A) LENGTH: 6
        (B) TYPE: amino acid
        (C) STRANDEDNESS: single
        (D) TOPOLOGY: linear (ix) FEATURE:
        (D) OTHER INFORMATION: Xaa at position 2 is D-
            Tryptophan (xi) SEQUENCE DESCRIPTION: SEQ ID NO: 40:

Tyr Xaa Lys Val Cys Thr
 1               5

(2) INFORMATION FOR SEQ ID NO: 41:

(i) SEQUENCE CHARACTERISTICS:
        (A) LENGTH: 6
        (B) TYPE: amino acid
        (C) STRANDEDNESS: single
        (D) TOPOLOGY: linear (ix) FEATURE:
        (D) OTHER INFORMATION: Xaa at position 2 is D-
            Tryptophan (xi) SEQUENCE DESCRIPTION: SEQ ID NO: 41:

Tyr Xaa Lys Val Cys Phe
 1               5

(2) INFORMATION FOR SEQ ID NO: 42:

(i) SEQUENCE CHARACTERISTICS:
        (A) LENGTH: 6
        (B) TYPE: amino acid
        (C) STRANDEDNESS: single
        (D) TOPOLOGY: linear (ix) FEATURE:
        (D) OTHER INFORMATION: Xaa at position 2 is D-
            Tryptophan;
            Xaa at position 6 is
            pseudouridine-Cl-Phenylalanine (xi) SEQUENCE DESCRIPTION: SEQ ID NO: 42:

Tyr Xaa Lys Val Cys Xaa (2) INFORMATION FOR SEQ ID NO: 43:

(i) SEQUENCE CHARACTERISTICS:
        (A) LENGTH: 6
        (B) TYPE: amino acid
        (C) STRANDEDNESS: single
        (D) TOPOLOGY: linear (ix) FEATURE:
        (D) OTHER INFORMATION: Xaa at position 2 is D-Tryptophan;
        Xaa at position 6 is beta-Napthalalanine (xi) SEQUENCE DESCRIPTION: SEQ ID NO: 43:

Tyr Xaa Lys Val Cys Xaa
1                    5

(2) INFORMATION FOR SEQ ID NO: 44:

(i) SEQUENCE CHARACTERISTICS:
        (A) LENGTH: 8
        (B) TYPE: amino acid
        (C) STRANDEDNESS: single
        (D) TOPOLOGY: linear (ix) FEATURE:
        (D) OTHER INFORMATION: Xaa at position 1 is D-beta-Napthalalanine;
        Xaa at position 4 is D-Tryptophan (xi) SEQUENCE DESCRIPTION: SEQ ID NO: 44:

Xaa Cys Tyr Xaa Lys Val Cys Thr
1                    5

(2) INFORMATION FOR SEQ ID NO: 45:

(i) SEQUENCE CHARACTERISTICS:
        (A) LENGTH: 8
        (B) TYPE: amino acid
        (C) STRANDEDNESS: single
        (D) TOPOLOGY: linear (ix) FEATURE:
        (D) OTHER INFORMATION: Xaa at position 1 is D-Phenylalanine;
        Xaa at position 4 is D-Tryptophan;
        Xaa at position 6 is 2-Aminobutyric acid (xi) SEQUENCE DESCRIPTION: SEQ ID NO: 45:

Xaa Cys Tyr Xaa Lys Xaa Cys Thr
1                    5

(2) INFORMATION FOR SEQ ID NO: 46:

(i) SEQUENCE CHARACTERISTICS:
        (A) LENGTH: 8
        (B) TYPE: amino acid
        (C) STRANDEDNESS: single
        (D) TOPOLOGY: linear (ix) FEATURE:
        (D) OTHER INFORMATION: Xaa at position 1 is D-Phenylalanine;
        Xaa at position 4 is D-Tryptophan;
        Xaa at position 6 is 2-Aminobutyric acid Xaa at position 8 is
beta- Napthalalanine (xi) SEQUENCE DESCRIPTION: SEQ ID NO: 46:

Xaa  Cys  Tyr  Xaa  Lys  Xaa  Cys  Xaa
 1                   5

(2) INFORMATION FOR SEQ ID NO: 47:

(i) SEQUENCE CHARACTERISTICS:
        (A) LENGTH: 8
        (B) TYPE: amino acid
        (C) STRANDEDNESS: single
        (D) TOPOLOGY: linear (ix) FEATURE:
        (D) OTHER INFORMATION: Xaa at position 1 is D-
            Phenylalanine;
            Xaa at position 4 is D-
            Tryptophan (xi) SEQUENCE DESCRIPTION: SEQ ID NO: 47:

Xaa  Cys  Tyr  Xaa  Lys  Val  Cys  Thr
 1                   5

(2) INFORMATION FOR SEQ ID NO: 48:

(i) SEQUENCE CHARACTERISTICS:
        (A) LENGTH: 8
        (B) TYPE: amino acid
        (C) STRANDEDNESS: single
        (D) TOPOLOGY: linear (ix) FEATURE:
        (D) OTHER INFORMATION: Xaa at position 1 is
            D-beta- Napthalalanine;
            Xaa at position 3 is
            pentafluoro- Phenylalanine;
            Xaa at position 4 is D-
            Tryptophan (xi) SEQUENCE DESCRIPTION: SEQ ID NO: 48:

Xaa  Cys  Xaa  Xaa  Lys  Val  Cys  Thr
 1                   5

(2) INFORMATION FOR SEQ ID NO: 49:

(i) SEQUENCE CHARACTERISTICS:
        (A) LENGTH: 8
        (B) TYPE: amino acid
        (C) STRANDEDNESS: single
        (D) TOPOLOGY: linear (ix) FEATURE:
        (D) OTHER INFORMATION: Xaa at position 1 is
            D-beta- Napthalalanine;
            Xaa at position 4 is D-
            Tryptophan;
            Xaa at position 8 is
            beta- Napthalalanine (xi) SEQUENCE DESCRIPTION: SEQ ID NO: 49:

Xaa  Cys  Tyr  Xaa  Lys  Val  Cys  Xaa
 1                   5

(2) INFORMATION FOR SEQ ID NO: 50:

(i) SEQUENCE CHARACTERISTICS:
        (A) LENGTH: 8
        (B) TYPE: amino acid
        (C) STRANDEDNESS: single
        (D) TOPOLOGY: linear ( i x ) FEATURE:
    ( D ) OTHER INFORMATION: Xaa at position 1 is D-
        Phenylalanine;
        Xaa at position 4 is D-
        Tryptophan;
        Xaa at position 8 is
        beta- Napthalalanine ( x i ) SEQUENCE DESCRIPTION: SEQ ID NO: 50:

Xaa Cys Tyr Xaa Lys Val Cys Xaa
 1               5

( 2 ) INFORMATION FOR SEQ ID NO: 51:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is
            D-beta- Napthalalanine;
            Xaa at position 4 is D-
            Tryptophan;
            Xaa at position 6 is 2-
            Aminobutyric acid ( x i ) SEQUENCE DESCRIPTION: SEQ ID NO: 51:

Xaa Cys Tyr Xaa Lys Xaa Cys Thr
 1               5

( 2 ) INFORMATION FOR SEQ ID NO: 52:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-
            pseudouridine-Cl-Phenylalanine;
            Xaa at position 4 is
            D- Tryptophan;
            Xaa at position 6 is 2-
            Aminobutyric acid ( x i ) SEQUENCE DESCRIPTION: SEQ ID NO: 52:

Xaa Cys Tyr Xaa Lys Xaa Cys Thr
 1               5

( 2 ) INFORMATION FOR SEQ ID NO: 53:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-
            Phenylalanine;
            Xaa at position 3 is
            beta- Napthalalanine;
            Xaa at position 4 is D-
            Tryptophan ( x i ) SEQUENCE DESCRIPTION: SEQ ID NO: 53:

Xaa Cys Xaa Xaa Lys Val Cys Thr
 1               5

( 2 ) INFORMATION FOR SEQ ID NO: 54:

( i ) SEQUENCE CHARACTERISTICS:
           ( A ) LENGTH: 7
           ( B ) TYPE: amino acid
           ( C ) STRANDEDNESS: single
           ( D ) TOPOLOGY: linear ( i x ) FEATURE:
           ( D ) OTHER INFORMATION: Xaa at position 1 is D-
               Phenylalanine;
               Xaa at position 4 is D-
               Tryptophan ( x i ) SEQUENCE DESCRIPTION: SEQ ID NO: 54:

Xaa  Cys  Tyr  Xaa  Lys  Cys  Thr
 1                      5

( 2 ) INFORMATION FOR SEQ ID NO: 55:

( i ) SEQUENCE CHARACTERISTICS:
           ( A ) LENGTH: 7
           ( B ) TYPE: amino acid
           ( C ) STRANDEDNESS: single
           ( D ) TOPOLOGY: linear ( i x ) FEATURE:
           ( D ) OTHER INFORMATION: Xaa at position 3 is D-
               Phenylalanine;
               Xaa at position 4 is D-
               Tryptophan;

( x i ) SEQUENCE DESCRIPTION: SEQ ID NO: 55:

Pro  Phe  Xaa  Xaa  Lys  Thr  Phe
 1                      5

( 2 ) INFORMATION FOR SEQ ID NO: 56:

( i ) SEQUENCE CHARACTERISTICS:
           ( A ) LENGTH: 6
           ( B ) TYPE: amino acid
           ( C ) STRANDEDNESS: single
           ( D ) TOPOLOGY: linear ( i x ) FEATURE:
           ( D ) OTHER INFORMATION: Xaa at position 3 is D-
               Tryptophan;
               Xaa at position 6 is N-Me-
               Phenylalanine ( x i ) SEQUENCE DESCRIPTION: SEQ ID NO: 56:

Pro  Phe  Xaa  Lys  Thr  Xaa
 1                  5

( 2 ) INFORMATION FOR SEQ ID NO: 57:

( i ) SEQUENCE CHARACTERISTICS:
           ( A ) LENGTH: 6
           ( B ) TYPE: amino acid
           ( C ) STRANDEDNESS: single
           ( D ) TOPOLOGY: linear ( i x ) FEATURE:
           ( D ) OTHER INFORMATION: Xaa at position 1 is N-Me-
               Alanine;
               Xaa at position 3 is D-
               Tryptophan ( x i ) SEQUENCE DESCRIPTION: SEQ ID NO: 57:

Xaa  Tyr  Xaa  Lys  Thr  Phe
 1                  5

( 2 ) INFORMATION FOR SEQ ID NO: 58:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-Tryptophan ( x i ) SEQUENCE DESCRIPTION: SEQ ID NO: 58:

Pro  Tyr  Xaa  Lys  Thr  Phe
 1                        5

( 2 ) INFORMATION FOR SEQ ID NO: 59:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-Tryptophan ( x i ) SEQUENCE DESCRIPTION: SEQ ID NO: 59:

Pro  Tyr  Xaa  Lys  Thr  Phe
 1                        5

( 2 ) INFORMATION FOR SEQ ID NO: 60:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is L-Tryptophan ( x i ) SEQUENCE DESCRIPTION: SEQ ID NO: 60:

Pro  Phe  Xaa  Lys  Thr  Phe
 1                        5

( 2 ) INFORMATION FOR SEQ ID NO: 61:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-Tryptophan (F)

( x i ) SEQUENCE DESCRIPTION: SEQ ID NO: 61:

Pro  Phe  Xaa  Lys  Thr  Phe
 1                        5

( 2 ) INFORMATION FOR SEQ ID NO: 62:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
            ( D ) OTHER INFORMATION: Xaa at position 3 is Tryptophan
            ( F )

( x i ) SEQUENCE DESCRIPTION: SEQ ID NO: 62:

Pro Phe Xaa Lys Thr Phe
 1                   5

( 2 ) INFORMATION FOR SEQ ID NO: 63:

( i ) SEQUENCE CHARACTERISTICS:
            ( A ) LENGTH: 6
            ( B ) TYPE: amino acid
            ( C ) STRANDEDNESS: single
            ( D ) TOPOLOGY: linear ( i x ) FEATURE:
            ( D ) OTHER INFORMATION: Xaa at position 3 is D-
                    Tryptophan ( x i ) SEQUENCE DESCRIPTION: SEQ ID NO: 63:

Pro Phe Xaa Lys Ser Phe
 1                   5

( 2 ) INFORMATION FOR SEQ ID NO: 64:

( i ) SEQUENCE CHARACTERISTICS:
            ( A ) LENGTH: 6
            ( B ) TYPE: amino acid
            ( C ) STRANDEDNESS: single
            ( D ) TOPOLOGY: linear ( i x ) FEATURE:
            ( D ) OTHER INFORMATION: Xaa at position 3 is D-
                    Tryptophan;
                    Xaa at position 6 is
                    pseudouridine-Phenylalanine ( x i ) SEQUENCE DESCRIPTION: SEQ ID NO: 64:

Pro Phe Xaa Lys Thr Xaa
 1                   5

( 2 ) INFORMATION FOR SEQ ID NO: 65:

( i ) SEQUENCE CHARACTERISTICS:
            ( A ) LENGTH: 6
            ( B ) TYPE: amino acid
            ( C ) STRANDEDNESS: single
            ( D ) TOPOLOGY: linear ( i x ) FEATURE:
            ( D ) OTHER INFORMATION: Xaa at position 1 is D-Alanine;
                    Xaa at position 2 is N-Me-D-
                    Phenylalanine;
                    Xaa at position 3 is
                    D- Threonine;
                    Xaa at position 4 is D-Lysine;
                    Xaa at position 6 is D-
                    Phenylalanine ( x i ) SEQUENCE DESCRIPTION: SEQ ID NO: 65:

Xaa Xaa Xaa Xaa Trp Phe
 1                   5

( 2 ) INFORMATION FOR SEQ ID NO: 66:

( i ) SEQUENCE CHARACTERISTICS:
            ( A ) LENGTH: 6
            ( B ) TYPE: amino acid
            ( C ) STRANDEDNESS: single
            ( D ) TOPOLOGY: linear ( i x ) FEATURE:
  ( D ) OTHER INFORMATION: Xaa at position 1 is D-Alanine;
    Xaa at position 2 is N-Me-D-Phenylalanine;
    Xaa at position 3 is D-Valine;
    Xaa at position 5 is D-Tryptophan;
    Xaa at position 6 is D-Phenylalanine ( x i ) SEQUENCE DESCRIPTION: SEQ ID NO: 66:

Xaa Xaa Xaa Lys Xaa Xaa
 1               5

( 2 ) INFORMATION FOR SEQ ID NO: 67:

( i ) SEQUENCE CHARACTERISTICS:
    ( A ) LENGTH: 6
    ( B ) TYPE: amino acid
    ( C ) STRANDEDNESS: single
    ( D ) TOPOLOGY: linear ( i x ) FEATURE:
    ( D ) OTHER INFORMATION: Xaa at position 1 is D-Alanine;
      Xaa at position 2 is N-Me-D-Phenylalanine;
      Xaa at position 3 is D-Tryptophan;
      Xaa at position 5 is D-Tryptophan;
      Xaa at position 6 is D-Phenylalanine ( x i ) SEQUENCE DESCRIPTION: SEQ ID NO: 67:

Xaa Xaa Xaa Lys Xaa Xaa
 1               5

( 2 ) INFORMATION FOR SEQ ID NO: 68:

( i ) SEQUENCE CHARACTERISTICS:
    ( A ) LENGTH: 6
    ( B ) TYPE: amino acid
    ( C ) STRANDEDNESS: single
    ( D ) TOPOLOGY: linear ( i x ) FEATURE:
    ( D ) OTHER INFORMATION: Xaa at position 1 is D-2-Aminobutyric acid;
      Xaa at position 2 is N-Me-D-Phenylalanine;
      Xaa at position 3 is D-Valine;
      Xaa at position 5 is D-Tryptophan;
      Xaa at position 6 is D-Tyrosine ( x i ) SEQUENCE DESCRIPTION: SEQ ID NO: 68:

Xaa Xaa Xaa Lys Xaa Xaa
 1               5

( 2 ) INFORMATION FOR SEQ ID NO: 69:

( i ) SEQUENCE CHARACTERISTICS:
    ( A ) LENGTH: 6
    ( B ) TYPE: amino acid
    ( C ) STRANDEDNESS: single
    ( D ) TOPOLOGY: linear ( i x ) FEATURE:
    ( D ) OTHER INFORMATION: Xaa at position 1 is N-Me-Alanine;
      Xaa at position 3 is D-Tryptophan ( x i ) SEQUENCE DESCRIPTION: SEQ ID NO: 69:

Xaa Tyr Xaa Lys Val Phe
 1               5

( 2 ) INFORMATION FOR SEQ ID NO: 70:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-
            Tryptophan;
            Xaa at position 4 is 4-Amphe-
            Threonine ( x i ) SEQUENCE DESCRIPTION: SEQ ID NO: 70:

Pro Tyr Xaa Xaa Thr Phe
 1               5

( 2 ) INFORMATION FOR SEQ ID NO: 71:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-
            Tryptophan;
            Xaa at position 4 is 4-Amphe-
            Threonine ( x i ) SEQUENCE DESCRIPTION: SEQ ID NO: 71:

Pro Phe Xaa Xaa Thr Phe
 1               5

( 2 ) INFORMATION FOR SEQ ID NO: 72:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is N-Me-
            Alanine;
            Xaa at position 3 is D-
            Tryptophan;
            Xaa at position 4 is 4-Amphe-
            Threonine ( x i ) SEQUENCE DESCRIPTION: SEQ ID NO: 72:

Xaa Tyr Xaa Xaa Thr Phe
 1               5

( 2 ) INFORMATION FOR SEQ ID NO: 73:

( i ) SEQUENCE CHARACTERISTICS:
        ( A ) LENGTH: 7
        ( B ) TYPE: amino acid
        ( C ) STRANDEDNESS: single
        ( D ) TOPOLOGY: linear ( i x ) FEATURE:
        ( D ) OTHER INFORMATION: Xaa at position 4 is D-
            Tryptophan ( x i ) SEQUENCE DESCRIPTION: SEQ ID NO: 73:

Asn  Phe  Phe  Xaa  Lys  Thr  Phe
 1                    5

( 2 ) INFORMATION FOR SEQ ID NO: 74:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-
            Tryptophan ( x i ) SEQUENCE DESCRIPTION: SEQ ID NO: 74:

Asn  Phe  Xaa  Lys  Thr  Phe
 1                5

( 2 ) INFORMATION FOR SEQ ID NO: 75:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 4 is D-
            Tryptophan;
            Xaa at position 8 is beta-
            Alanine ( x i ) SEQUENCE DESCRIPTION: SEQ ID NO: 75:

Asn  Phe  Phe  Xaa  Lys  Thr  Phe  Xaa
 1                     5

( 2 ) INFORMATION FOR SEQ ID NO: 76:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 4 is D-
            Tryptophan;
            Xaa at position 8 is D-Glutamic
            acid ( x i ) SEQUENCE DESCRIPTION: SEQ ID NO: 76:

Asn  Phe  Phe  Xaa  Lys  Thr  Phe  Xaa
 1                     5

( 2 ) INFORMATION FOR SEQ ID NO: 77:

( i ) SEQUENCE CHARACTERISTICS:
        ( A ) LENGTH: 6
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-
            Tryptophan ( x i ) SEQUENCE DESCRIPTION: SEQ ID NO: 77:

Phe  Phe  Xaa  Lys  Thr  Phe
 1                5

( 2 ) INFORMATION FOR SEQ ID NO: 78:

( i ) SEQUENCE CHARACTERISTICS:
    ( A ) LENGTH: 7
    ( B ) TYPE: amino acid
    ( C ) STRANDEDNESS: single
    ( D ) TOPOLOGY: linear ( i x ) FEATURE:
    ( D ) OTHER INFORMATION: Xaa at position 3 is D-Tryptophan ( x i ) SEQUENCE DESCRIPTION: SEQ ID NO: 78:

```
Phe  Phe  Xaa  Lys  Thr  Phe  Gly
 1                 5
```

( 2 ) INFORMATION FOR SEQ ID NO: 79:

( i ) SEQUENCE CHARACTERISTICS:
    ( A ) LENGTH: 8
    ( B ) TYPE: amino acid
    ( C ) STRANDEDNESS: single
    ( D ) TOPOLOGY: linear ( i x ) FEATURE:
    ( D ) OTHER INFORMATION: Xaa at position 4 is D-Tryptophan ( x i ) SEQUENCE DESCRIPTION: SEQ ID NO: 79:

```
Asn  Phe  Phe  Xaa  Lys  Thr  Phe  Gly
 1                      5
```

( 2 ) INFORMATION FOR SEQ ID NO: 80:

( i ) SEQUENCE CHARACTERISTICS:
    ( A ) LENGTH: 7
    ( B ) TYPE: amino acid
    ( C ) STRANDEDNESS: single
    ( D ) TOPOLOGY: linear ( i x ) FEATURE:
    ( D ) OTHER INFORMATION: Xaa at position 4 is D-Tryptophan (F)

( x i ) SEQUENCE DESCRIPTION: SEQ ID NO: 80:

```
Asn  Phe  Phe  Xaa  Lys  Thr  Phe
 1                 5
```

( 2 ) INFORMATION FOR SEQ ID NO: 81:

( i ) SEQUENCE CHARACTERISTICS:
    ( A ) LENGTH: 7
    ( B ) TYPE: amino acid
    ( C ) STRANDEDNESS: single
    ( D ) TOPOLOGY: linear ( i x ) FEATURE:
    ( D ) OTHER INFORMATION: Xaa at position 4 is D-Tryptophan ($NO_2$)

( x i ) SEQUENCE DESCRIPTION: SEQ ID NO: 81:

```
Asn  Phe  Phe  Xaa  Lys  Thr  Phe
 1                 5
```

( 2 ) INFORMATION FOR SEQ ID NO: 82:

( i ) SEQUENCE CHARACTERISTICS:
    ( A ) LENGTH: 7
    ( B ) TYPE: amino acid
    ( C ) STRANDEDNESS: single (D) TOPOLOGY: linear (ix) FEATURE:
(D) OTHER INFORMATION: Xaa at position 4 is Tryptophan
(Br)

(xi) SEQUENCE DESCRIPTION: SEQ ID NO: 82:

Asn Phe Phe Xaa Lys Thr Phe
1               5

(2) INFORMATION FOR SEQ ID NO: 83:

(i) SEQUENCE CHARACTERISTICS:
(A) LENGTH: 7
(B) TYPE: amino acid
(C) STRANDEDNESS: single
(D) TOPOLOGY: linear (ix) FEATURE:
(D) OTHER INFORMATION: Xaa at position 4 is D-Tryptophan;
Xaa at position 7 is
Phenylalanine (I)

(xi) SEQUENCE DESCRIPTION: SEQ ID NO: 83:

Asn Phe Phe Xaa Lys Thr Xaa
1               5

(2) INFORMATION FOR SEQ ID NO: 84:

(i) SEQUENCE CHARACTERISTICS:
(A) LENGTH: 7
(B) TYPE: amino acid
(C) STRANDEDNESS: single
(D) TOPOLOGY: linear (ix) FEATURE:
(D) OTHER INFORMATION: Xaa at position 4 is
D- Tryptophan;
Xaa at position 7 is Tyrosine
(But)

(xi) SEQUENCE DESCRIPTION: SEQ ID NO: 84:

Asn Phe Phe Xaa Lys Thr Xaa
1               5

(2) INFORMATION FOR SEQ ID NO: 85:

(i) SEQUENCE CHARACTERISTICS:
(A) LENGTH: 11
(B) TYPE: amino acid
(C) STRANDEDNESS: single
(D) TOPOLOGY: linear (ix) FEATURE:
(D) OTHER INFORMATION: Xaa at position 5 is D-Tryptophan (xi) SEQUENCE DESCRIPTION: SEQ ID NO: 85:

Lys Asn Phe Phe Xaa Lys Thr Phe Thr Pro Cys
1               5                   10

(2) INFORMATION FOR SEQ ID NO: 86:

(i) SEQUENCE CHARACTERISTICS:
(A) LENGTH: 11
(B) TYPE: amino acid
(C) STRANDEDNESS: single
(D) TOPOLOGY: linear (ix) FEATURE:
(D) OTHER INFORMATION: Xaa at position 5 is D-

Tryptophan;
Xaa at position 10 is Tpo ( x i ) SEQUENCE DESCRIPTION: SEQ ID NO: 86:

Lys Asn Phe Phe Xaa Lys Thr Phe Thr Xaa Cys
1               5                   10

( 2 ) INFORMATION FOR SEQ ID NO: 87:

( i ) SEQUENCE CHARACTERISTICS:
        ( A ) LENGTH: 11
        ( B ) TYPE: amino acid
        ( C ) STRANDEDNESS: single
        ( D ) TOPOLOGY: linear ( i x ) FEATURE:
        ( D ) OTHER INFORMATION: Xaa at position 5 is D-
Tryptophan;
Xaa at position 10 is Me-Leucine ( x i ) SEQUENCE DESCRIPTION: SEQ ID NO: 87:

Lys Asn Phe Phe Xaa Lys Thr Phe Thr Xaa Cys
1               5                   10

( 2 ) INFORMATION FOR SEQ ID NO: 88:

( i ) SEQUENCE CHARACTERISTICS:
        ( A ) LENGTH: 7
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-
Tryptophan ( x i ) SEQUENCE DESCRIPTION: SEQ ID NO: 88:

Phe Phe Xaa Lys Thr Phe Phe
1               5

( 2 ) INFORMATION FOR SEQ ID NO: 89:

( i ) SEQUENCE CHARACTERISTICS:
        ( A ) LENGTH: 7
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-
Tryptophan;
Xaa at position 7 is D-
Phenylalanine ( x i ) SEQUENCE DESCRIPTION: SEQ ID NO: 89:

Phe Phe Xaa Lys Thr Phe Xaa
1               5

( 2 ) INFORMATION FOR SEQ ID NO: 90:

( i ) SEQUENCE CHARACTERISTICS:
        ( A ) LENGTH: 7
        ( B ) TYPE: amino acid
        ( C ) STRANDEDNESS: single
        ( D ) TOPOLOGY: linear ( i x ) FEATURE:
        ( D ) OTHER INFORMATION: Xaa at position 3 is D-
Tryptophan (5F)

( x i ) SEQUENCE DESCRIPTION: SEQ ID NO: 90:

```
Phe  Phe  Xaa  Lys  Thr  Phe  Phe
 1                 5
```

(2) INFORMATION FOR SEQ ID NO: 91:

(i) SEQUENCE CHARACTERISTICS:
        (A) LENGTH: 7
        (B) TYPE: amino acid
        (C) STRANDEDNESS: single
        (D) TOPOLOGY: linear (ix) FEATURE:
        (D) OTHER INFORMATION: Xaa at position 4 is D-
            Tryptophan;
            Xaa at position 5 is Lysine (Ac)

(xi) SEQUENCE DESCRIPTION: SEQ ID NO: 91:

```
Asn  Phe  Phe  Xaa  Xaa  Thr  Phe
 1                 5
```

(2) INFORMATION FOR SEQ ID NO: 92:

(i) SEQUENCE CHARACTERISTICS:
        (A) LENGTH: 7
        (B) TYPE: amino acid
        (C) STRANDEDNESS: single
        (D) TOPOLOGY: linear (ix) FEATURE:
        (D) OTHER INFORMATION: Xaa at position 4 is D-
            Tryptophan (xi) SEQUENCE DESCRIPTION: SEQ ID NO: 92:

```
Lys  Phe  Phe  Xaa  Lys  Thr  Phe
 1                 5
```

(2) INFORMATION FOR SEQ ID NO: 93:

(i) SEQUENCE CHARACTERISTICS:
        (A) LENGTH: 7
        (B) TYPE: amino acid
        (C) STRANDEDNESS: single
        (D) TOPOLOGY: linear (ix) FEATURE:
        (D) OTHER INFORMATION: Xaa at position 1 is Ornithine;
            Xaa at position 4 is D-
            Tryptophan (xi) SEQUENCE DESCRIPTION: SEQ ID NO: 93:

```
Xaa  Phe  Phe  Xaa  Lys  Thr  Phe
 1                 5
```

(2) INFORMATION FOR SEQ ID NO:94:

(i) SEQUENCE CHARACTERISTICS:
        (A) LENGTH: 9
        (B) TYPE: amino acid
        (C) STRANDEDNESS: single
        (D) TOPOLOGY: linear (ix) FEATURE:
        (D) OTHER INFORMATION: Xaa at position 1 is D-
            Phenylalanine;
            Xaa at position 5 is D-
            Tryptophan (xi) SEQUENCE DESCRIPTION: SEQ ID NO: 94:

```
Xaa  Cys  Tyr  Tyr  Xaa  Lys  Val  Cys  Thr
 1                 5
```

( 2 ) INFORMATION FOR SEQ ID NO: 95:

( i ) SEQUENCE CHARACTERISTICS:
　　　　( A ) LENGTH: 8
　　　　( B ) TYPE: amino acid
　　　　( C ) STRANDEDNESS: single
　　　　( D ) TOPOLOGY: linear ( i x ) FEATURE:
　　　　( D ) OTHER INFORMATION: Xaa at position 1 is
　　　　　　D- Napthalalanine;
　　　　　　Xaa at position 4 is D-
　　　　　　Tryptophan;
　　　　　　Xaa at position 8 is
　　　　　　Napthalalanine ( x i ) SEQUENCE DESCRIPTION: SEQ ID NO: 95:

Xaa Cys Tyr Xaa Lys Thr Cys Xaa
 1                   5

( 2 ) INFORMATION FOR SEQ ID NO: 96:

( i ) SEQUENCE CHARACTERISTICS:
　　　　( A ) LENGTH: 8
　　　　( B ) TYPE: amino acid
　　　　( C ) STRANDEDNESS: single
　　　　( D ) TOPOLOGY: linear ( i x ) FEATURE:
　　　　( D ) OTHER INFORMATION: Xaa at position 1 is
　　　　　　D- Napthalalanine;
　　　　　　Xaa at position 4 is D-
　　　　　　Tryptophan ( x i ) SEQUENCE DESCRIPTION: SEQ ID NO: 96:

Xaa Cys Tyr Xaa Lys Thr Cys Thr
 1                   5

( 2 ) INFORMATION FOR SEQ ID NO: 97:

( i ) SEQUENCE CHARACTERISTICS:
　　　　( A ) LENGTH: 8
　　　　( B ) TYPE: amino acid
　　　　( C ) STRANDEDNESS: single
　　　　( D ) TOPOLOGY: linear ( i x ) FEATURE:
　　　　( D ) OTHER INFORMATION: Xaa at position 1 is D-
　　　　　　Phenylalanine;
　　　　　　Xaa at position 4 is D-
　　　　　　Tryptophan;
　　　　　　Xaa at position 6 is 2-
　　　　　　Aminobutyric acid ( x i ) SEQUENCE DESCRIPTION: SEQ ID NO: 97:

Xaa Cys Tyr Xaa Lys Xaa Cys Thr
 1                   5

( 2 ) INFORMATION FOR SEQ ID NO: 98:

( i ) SEQUENCE CHARACTERISTICS:
　　　　( A ) LENGTH: 8
　　　　( B ) TYPE: amino acid
　　　　( C ) STRANDEDNESS: single
　　　　( D ) TOPOLOGY: linear ( i x ) FEATURE:
　　　　( D ) OTHER INFORMATION: Xaa at position 1 is D-
　　　　　　Phenylalanine;
　　　　　　Xaa at position 4 is D-
　　　　　　Tryptophan;
　　　　　　Xaa at position 8 is
　　　　　　Napthalalanine (x i) SEQUENCE DESCRIPTION: SEQ ID NO: 98:

Xaa Cys Tyr Xaa Lys Thr Cys Xaa
1                   5

(2) INFORMATION FOR SEQ ID NO: 99:

(i) SEQUENCE CHARACTERISTICS:
  (A) LENGTH: 8
  (B) TYPE: amino acid
  (C) STRANDEDNESS: single
  (D) TOPOLOGY: linear (i x) FEATURE:
  (D) OTHER INFORMATION: Xaa at position 1 is D-
   Phenylalanine;
   Xaa at position 4 is D-
   Tryptophan (x i) SEQUENCE DESCRIPTION: SEQ ID NO: 99:

Xaa Cys Tyr Xaa Lys Thr Cys Thr
1                   5

(2) INFORMATION FOR SEQ ID NO: 100:

(i) SEQUENCE CHARACTERISTICS:
  (A) LENGTH: 8
  (B) TYPE: amino acid
  (C) STRANDEDNESS: single
  (D) TOPOLOGY: linear (i x) FEATURE:
  (D) OTHER INFORMATION: Xaa at position 1 is D-
   Phenylalanine;
   Xaa at position 2 is
   pseudouridine-chloro-
   Phenylalanine;
   Xaa at position 4 is D-
   Tryptophan (x i) SEQUENCE DESCRIPTION: SEQ ID NO: 100:

Xaa Xaa Tyr Xaa Lys Thr Phe Thr
1                   5

(2) INFORMATION FOR SEQ ID NO: 101:

(i) SEQUENCE CHARACTERISTICS:
  (A) LENGTH: 9
  (B) TYPE: amino acid
  (C) STRANDEDNESS: single
  (D) TOPOLOGY: linear (i x) FEATURE:
  (D) OTHER INFORMATION: Xaa at position 1 is D-
   Phenylalanine;
   Xaa at position 2 is
   pseudouridine-(NO$_2$)-
   Phenylalanine;
   Xaa at position 5 is
   D- Tryptophan (x i) SEQUENCE DESCRIPTION: SEQ ID NO: 101:

Xaa Xaa Phe Tyr Xaa Lys Val Phe Thr
1                   5

(2) INFORMATION FOR SEQ ID NO: 102:

(i) SEQUENCE CHARACTERISTICS:
  (A) LENGTH: 8
  (B) TYPE: amino acid
  (C) STRANDEDNESS: single
  (D) TOPOLOGY: linear ( i x ) FEATURE:
　　　　　　　　( D ) OTHER INFORMATION: Xaa at position 1 is
　　　　　　　　　　　D- Napthalalanine;
　　　　　　　　　　　Xaa at position 2 is
　　　　　　　　　　　pseudouridine-chloro-
　　　　　　　　　　　Phenylanine;
　　　　　　　　　　　Xaa at position 4 is D-
　　　　　　　　　　　Tryptophan ( x i ) SEQUENCE DESCRIPTION: SEQ ID NO: 102:

Xaa　Xaa　Tyr　Xaa　Lys　Val　Phe　Thr
 1                    5

( 2 ) INFORMATION FOR SEQ ID NO: 103:

( i ) SEQUENCE CHARACTERISTICS:
　　　　　　　　( A ) LENGTH: 8
　　　　　　　　( B ) TYPE: amino acid
　　　　　　　　( C ) STRANDEDNESS: single
　　　　　　　　( D ) TOPOLOGY: linear ( i x ) FEATURE:
　　　　　　　　( D ) OTHER INFORMATION: Xaa at position 1 is D-
　　　　　　　　　　　Phenylalanine;
　　　　　　　　　　　Xaa at position 4 is D-
　　　　　　　　　　　Tryptophan ( x i ) SEQUENCE DESCRIPTION: SEQ ID NO: 103:

Xaa　Phe　Phe　Xaa　Lys　Thr　Phe　Thr
 1                    5

( 2 ) INFORMATION FOR SEQ ID NO: 104:

( i ) SEQUENCE CHARACTERISTICS:
　　　　　　　　( A ) LENGTH: 8
　　　　　　　　( B ) TYPE: amino acid
　　　　　　　　( C ) STRANDEDNESS: single
　　　　　　　　( D ) TOPOLOGY: linear ( i x ) FEATURE:
　　　　　　　　( D ) OTHER INFORMATION: Xaa at position 1 is D-
　　　　　　　　　　　Phenylalanine;
　　　　　　　　　　　Xaa at position 4 is D-
　　　　　　　　　　　Tryptophan ( x i ) SEQUENCE DESCRIPTION: SEQ ID NO: 104:

Xaa　Phe　Tyr　Xaa　Lys　Val　Phe　Thr
 1                    5

( 2 ) INFORMATION FOR SEQ ID NO: 105:

( i ) SEQUENCE CHARACTERISTICS:
　　　　　　　　( A ) LENGTH: 8
　　　　　　　　( B ) TYPE: amino acid
　　　　　　　　( C ) STRANDEDNESS: single
　　　　　　　　( D ) TOPOLOGY: linear ( i x ) FEATURE:
　　　　　　　　( D ) OTHER INFORMATION: Xaa at position 1 is D-
　　　　　　　　　　　Phenylalanine;
　　　　　　　　　　　Xaa at position 2 is
　　　　　　　　　　　pseudouridine-chloro-
　　　　　　　　　　　Phenylalanine;
　　　　　　　　　　　Xaa at position 4 is D-
　　　　　　　　　　　Tryptophan ( x i ) SEQUENCE DESCRIPTION: SEQ ID NO: 105:

Xaa　Xaa　Tyr　Xaa　Lys　Val　Phe　Thr
 1                    5

( 2 ) INFORMATION FOR SEQ ID NO: 106:

( i ) SEQUENCE CHARACTERISTICS:
    ( A ) LENGTH: 8
    ( B ) TYPE: amino acid
    ( C ) STRANDEDNESS: single
    ( D ) TOPOLOGY: linear ( i x ) FEATURE:
    ( D ) OTHER INFORMATION: Xaa at position 1 is D-
        Phenylalanine;
        Xaa at position 4 is D-
        Tryptophan;
        Xaa at position 8 is
        D-beta- Napthalalanine ( x i ) SEQUENCE DESCRIPTION: SEQ ID NO: 106:

Xaa Ala Tyr Xaa Lys Val Ala Xaa
 1               5

( 2 ) INFORMATION FOR SEQ ID NO: 107:

( i ) SEQUENCE CHARACTERISTICS:
    ( A ) LENGTH: 27
    ( B ) TYPE: amino acid
    ( C ) STRANDEDNESS: single
    ( D ) TOPOLOGY: linear ( x i ) SEQUENCE DESCRIPTION: SEQ ID NO: 107:

Ala Pro Val Ser Val Gly Gly Gly Thr Val Leu Ala Lys Met Tyr Pro
 1               5                   10                  15

Arg Gly Asn His Trp Ala Val Gly His Leu Met
             20                  25

( 2 ) INFORMATION FOR SEQ ID NO: 108:

( i ) SEQUENCE CHARACTERISTICS:
    ( A ) LENGTH: 8
    ( B ) TYPE: amino acid
    ( C ) STRANDEDNESS: single
    ( D ) TOPOLOGY: linear ( i x ) FEATURE:
    ( D ) OTHER INFORMATION: Xaa at position 1 is
        D- Napthalalanine;
        Xaa at position 2 is c-Cysteine;
        Xaa at position 4 is D-
        Tryptophan ( x i ) SEQUENCE DESCRIPTION: SEQ ID NO: 108:

Xaa Xaa Tyr Xaa Lys Val Cys Thr
 1               5

( 2 ) INFORMATION FOR SEQ ID NO: 109:

( i ) SEQUENCE CHARACTERISTICS:
    ( A ) LENGTH: 8
    ( B ) TYPE: amino acid
    ( C ) STRANDEDNESS: single
    ( D ) TOPOLOGY: linear ( i x ) FEATURE:
    ( D ) OTHER INFORMATION: Xaa at position 1 is
        D- Napthalalanine;
        Xaa at position 2 is c-Cysteine;
        Xaa at position 4 is D-
        Tryptophan;
        Xaa at position 5 is Lysine
        ( B O C )

( x i ) SEQUENCE DESCRIPTION: SEQ ID NO: 109:

Xaa Xaa Tyr Xaa Xaa Val Cys Thr
 1               5

( 2 ) INFORMATION FOR SEQ ID NO: 110:

( i ) SEQUENCE CHARACTERISTICS:
       ( A ) LENGTH: 8
       ( B ) TYPE: amino acid
       ( C ) STRANDEDNESS: single
       ( D ) TOPOLOGY: linear ( i x ) FEATURE:
       ( D ) OTHER INFORMATION: Xaa at position 1 is
             D- Napthalalanine;
             Xaa at position 2 is c-Cysteine;
             Xaa at position 4 is D-
             Tryptophan ( x i ) SEQUENCE DESCRIPTION: SEQ ID NO: 110:

Xaa Xaa Tyr Xaa Lys Val Cys Thr
 1               5

( 2 ) INFORMATION FOR SEQ ID NO: 111:

( i ) SEQUENCE CHARACTERISTICS:
       ( A ) LENGTH: 8
       ( B ) TYPE: amino acid
       ( C ) STRANDEDNESS: single
       ( D ) TOPOLOGY: linear ( i x ) FEATURE:
       ( D ) OTHER INFORMATION: Xaa at position 1 is
             D- Napthalalanine;
             Xaa at position 2 is Cyclo-
             Cysteine;
             Xaa at position 4 is D-
             Tryptophan;
             Xaa at position 5 is Lysine
             ( B O C )

( x i ) SEQUENCE DESCRIPTION: SEQ ID NO: 111:

Xaa Xaa Tyr Xaa Xaa Val Cys Thr
 1               5

( 2 ) INFORMATION FOR SEQ ID NO: 112:

( i ) SEQUENCE CHARACTERISTICS:
       ( A ) LENGTH: 8
       ( B ) TYPE: amino acid
       ( C ) STRANDEDNESS: single
       ( D ) TOPOLOGY: linear ( i x ) FEATURE:
       ( D ) OTHER INFORMATION: Xaa at position 1 is D-
             Phenylalanine;
             Xaa at position 2 is c-Cysteine;
             Xaa at position 4 is D-
             Tryptophan;
             Xaa at position 6 is 2-
             Aminobutyric acid ( x i ) SEQUENCE DESCRIPTION: SEQ ID NO: 112:

Xaa Xaa Tyr Xaa Lys Xaa Cys Thr
 1               5

( 2 ) INFORMATION FOR SEQ ID NO: 113:

( i ) SEQUENCE CHARACTERISTICS:
       ( A ) LENGTH: 8
       ( B ) TYPE: amino acid
       ( C ) STRANDEDNESS: single
       ( D ) TOPOLOGY: linear ( i x ) FEATURE:
       ( D ) OTHER INFORMATION: Xaa at position 1 is D-
             Phenylalanine;

Xaa at position 2 is c-Cysteine;
Xaa at position 4 is D-
Tryptophan;
Xaa at position 8 is
Napthalalanine ( x i ) SEQUENCE DESCRIPTION: SEQ ID NO: 113:

Xaa Xaa Tyr Xaa Lys Thr Cys Xaa
 1                5

( 2 ) INFORMATION FOR SEQ ID NO: 114:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-
Phenylalanine;
Xaa at position 2 is c-Cysteine;
Xaa at position 3 is Tyrosine
( O B t );
Xaa at position 4 is D-
Tryptophan;
Xaa at position 5 is Lysine
( B O C );
Xaa at position 6 is Threonine
( O B t );
Xaa at position 8 is
Napthalalanine ( x i ) SEQUENCE DESCRIPTION: SEQ ID NO: :114:

Xaa Xaa Xaa Xaa Xaa Xaa Cys Xaa
 1                5

( 2 ) INFORMATION FOR SEQ ID NO: 115:

( i ) SEQUENCE CHARACTERISTICS:
        ( A ) LENGTH: 8
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-
Phenylalanine;
Xaa at position 2 is c-Cysteine;
Xaa at position 3 is Tyrosine
( t B u );
Xaa at position 4 is D-
Tryptophan;
Xaa at position 5 is Lysine
( B o c );
Xaa at position 6 is 2-
Aminobutyric acid;
Xaa at position 8 is Threonine
( t B u )

( x i ) SEQUENCE DESCRIPTION: SEQ ID NO: 115:

Xaa Xaa Xaa Xaa Xaa Xaa Cys Xaa
 1                5

( 2 ) INFORMATION FOR SEQ ID NO: 116:

( i ) SEQUENCE CHARACTERISTICS:
        ( A ) LENGTH: 9
        ( B ) TYPE: amino acid
        ( C ) STRANDEDNESS: single
        ( D ) TOPOLOGY: linear ( i x ) FEATURE:
        ( D ) OTHER INFORMATION: Xaa at position 1 is D-

Phenylalanine ( x i ) SEQUENCE DESCRIPTION: SEQ ID NO: 116:

Xaa Gln Trp Ala Val Gly His Leu Leu
1               5

THERAPEUTIC PEPTIDE DERIVATIVES

BACKGROUND OF THE INVENTION

This invention is a continuation-in-part of U.S. Ser. No. 104,194, filed Aug. 9, 1993 now abandoned.

This invention relates to therapeutic peptides.

Several attempts have been made to prolong the activity of biologically active peptides. For example, peptides have been chemically modified by synthetically adding sugar moieties to increase the period during which the peptide is active (Sandoz, WO 88/02756; Sandoz, WO 89/09786; DE 3910667 A1, EPO 0 374 089 A2 (1990); and Breipohl, U.S. Pat. No. 4,861,755 (1989)). The addition of cationic anchors (EPO 0 363 589 A2 (1990)) and lipid moieties (Whittaker, WO 91/09837; Jung, U.S. Pat. No. 4,837,303 (1989)) has also been used to increase the lifetime of the peptide.

SUMMARY OF THE INVENTION

In general, the present invention provides derivatives of biologically active peptides which contain one or more substituents separately bonded to an amino group located on the N-terminal end or a side chain of the peptide moiety. In this modified form, the derivatives have more potent and prolonged biological activity than the corresponding unmodified peptide.

The peptide derivatives are advantageous in that they are inexpensive, highly biocompatible, lack deleterious side effects, and are compatible with different forms of therapeutic administration. In particular, many of the derivatives which have somatostatin as the peptide moiety have improved greatly improved potency and selectivity compared to unmodified somatostatin.

In one aspect, the invention features a peptide derivative containing a biologically active peptide moiety and at least one substituent attached to the peptide moiety; the substituent is selected from the group including Compounds I, II, and III, where Compound I is:

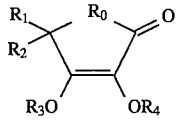

where:

$R_0$ is O, S, or $NR_5$, where $R_5$ is H or ($C_1$-$C_6$) alkyl; each $R_1$ and $R_2$, independently, is H, $(CH_2)_mOR_6$, or $CH(OR_7)CH_2OR_8$, where $R_6$ is H or ($C_2$-$C_7$) acyl, and each $R_7$ and $R_8$, independently, is H, ($C_2$-$C_7$) acyl, or $C(R_9)(R_{10})$, where each $R_9$ and $R_{10}$, independently, is H or ($C_1$-$C_6$) alkyl;

or each $R_1$ and $R_2$ is =$CHCH_2OR_{11}$, wherein in $R_{11}$, each $R_1$ and $R_2$, independently, is H or ($C_2$-$C_7$) acyl, and m is an integer between 1 and 5, inclusive; and one of $R_3$ or $R_4$ is $(CH_2)_nR_{12}$ or $(CH_2)_nCH(OH)R_{12}$, where $R_{12}$ is CO, $CH_2$, or $SO_2$, and n is an integer between 1 and 5, inclusive; and the remaining $R_3$ or $R_4$ is H, ($C_1$-$C_6$) hydroxyalkyl, or ($C_2$-$C_7$) acyl; and Compound II is:

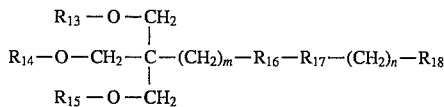

where:

each $R_{13}$, $R_{14}$ and $R_{15}$, independently, is H or ($C_2$-$C_{24}$) acyl;

$R_{16}$ is NH or absent;

$R_{17}$ is CO, O, or absent;

$R_{18}$ is CO, $CH_2$, $SO_2$, or absent; and m is an integer between 1 and 5, inclusive; and n is an integer between 0 and 5, inclusive; and Compound III is:

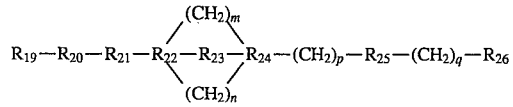

where:

$R_{19}$ is H, $NH_2$, an aromatic functional group, OH, ($C_1$-$C_6$) hydroxyalkyl, $H(R_{27})(R_{28})$, $SO_3H$, or absent where each $R_{27}$ and $R_{28}$, independently, is H or ($C_1$-$C_6$) alkyl;

$R_{20}$ is O or absent;

$R_{21}$ is ($C_1$-$C_6$)alkyl or absent;

$R_{22}$ is N, CH, O, or C;

-$R_{23}$- is ($C_1$-$C_6$)alkyl or absent;

$R_{24}$ is N, CH, or C;

$R_{25}$ is NH, O, or absent;

$R_{26}$ is $SO_2$, CO, $CH_2$, or absent;

m is an integer between 0 and 5, inclusive;

n is an integer between 0 and 5, inclusive;

p is an integer between 0 and 5, inclusive; and q is an integer between 0 and 5, inclusive.

In Compounds I, II and III the peptide moiety is attached to each of the substituents by a CO—N, $CH_2$—N, or $SO_2$—N bond between the substituent and a nitrogen atom of the N-terminus or a side chain of said peptide moiety.

In preferred embodiments, -$R_{23}$- is ($C_1$-$C_6$) alkyl; $R_{22}$ is N, C or CH; and $R_{24}$ is C. Alternatively, $R_{22}$ is O; $R_{19}$, $R_{20}$, $R_{21}$, and -$R_{23}$- are absent; and the sum of m and n is 3, 4, or 5.

In other preferred embodiments of the invention, the substituent is Compound I; in this embodiment, $R_{12}$ is preferably $CH_2$ or $SO_2$. Alternatively, the substituent may be Compound II, in which case $R_{18}$ is preferably $CH_2$ or $SO_2$; $R_{13}$, $R_{14}$, and $R_{15}$ are H; and $R_{17}$ is absent. In particularly preferred embodiments, the substituent is $(HOCH_2)_3C$—NH— $(CH)_2$—$SO_2$ or $(HOCH_2)_3C$—$CH_2$.

In still other embodiments of the invention, the substituent is Compound III; preferably, in this embodiment, -$R_{23}$- is absent and at least one of $R_{22}$ and $R_{24}$ is N. Alternatively, both $R_{22}$ and $R_{24}$ may be N.

In other embodiments, the substituent is one of:

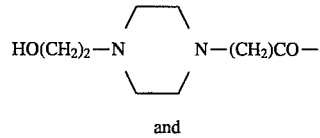

and

-continued

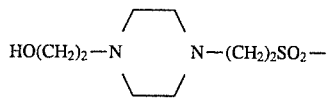

Preferably, the peptide moiety is selected from the group including: somatostatin, bombesin, calcitonin, calcitonin gene related peptide (CGRP), amylin, parathyroid hormone (PTH), gastrin releasing peptide (GRP), melanocyte stimulating hormone (MSH), adrenocorticotrophic hormone (ACTH), parathyroid related peptide (PTHrP), luteinizing hormone-releasing hormone (LHRH), growth hormone releasing factor (GHRF), growth hormone releasing peptide (GHRP), cholecystokinin (CCK), glucagon, Bradykinin, glucagon-like peptide (GLP), gastrin, enkephalin, neuromedins, endothelin, substance P, neuropeptide Y (NPY), peptide YY (PYY), vasoactive intestinal peptide (VIP), guanylin, pituitary adenylate cyclase activating polypeptide (PACAP), beta-cell tropin, adrenomedulin, and derivatives, fragments, and analogs thereof.

The peptide moiety is preferably somatostatin or a derivative, fragment, or analog thereof. Most preferably, the somatostatin analog is one of: H-D-Phe-c[Cys-Tyr-D-Trp-Lys-Abu-Cys]-Thr-NH$_2$, (SEQ. ID NO.1) H-D-Phe-c[Cys-Tyr-D-Trp-Lys-Thr-Cys]-Nal-NH$_2$, (SEQ. ID NO.1) and H-D-Nal-c[Cys-Tyr-D-Trp-Lys-Val-Cys]-Thr-NH$_2$ (SEQ. ID NO.3). Alternatively, the peptide moiety is bombesin or a derivative, fragment or analog thereof.

In still other preferred embodiments, the peptide derivative is one of:

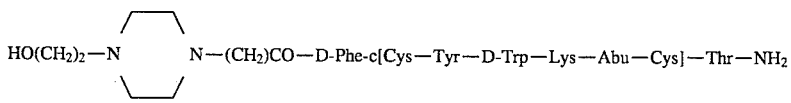

and

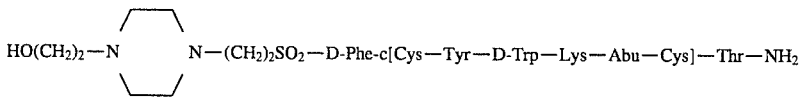

In another aspect, the invention provides a dimeric peptide derivative containing two biologically active peptide moieties, and at least one substituent attached to each of the peptide moieties. The substituent is selected from the group consisting of compounds IV and V, where compound IV has a generic structure equivalent to compound I, and compound V has a generic structure equivalent to compound III. In the dimer, each of the peptide moieties is attached to the substituents by a CO—N, CH$_2$—N, or SO$_2$—N bond between the substituent and a nitrogen atom of the N-terminus or a side chain of one of the peptide moieties.

In yet another aspect, the invention provides a method for treating a disease, such as cancer, in a patient; the method includes the step of administering to the patient a therapeutic amount of the peptide derivatives described herein. In preferred embodiments, the peptide moiety used in the treatment is somatostatin.

By "biologically active", as used herein, is meant a naturally occurring, recombinant, and synthetic peptide having physiological or therapeutic activity. In general, this term covers all derivatives, fragments, and analogs of biologically active peptides which exhibit a qualitatively similar or opposite effect to that of the unmodified peptide.

DESCRIPTION OF THE PREFERRED EMBODIMENTS

Peptide Derivatives

Figure 1:
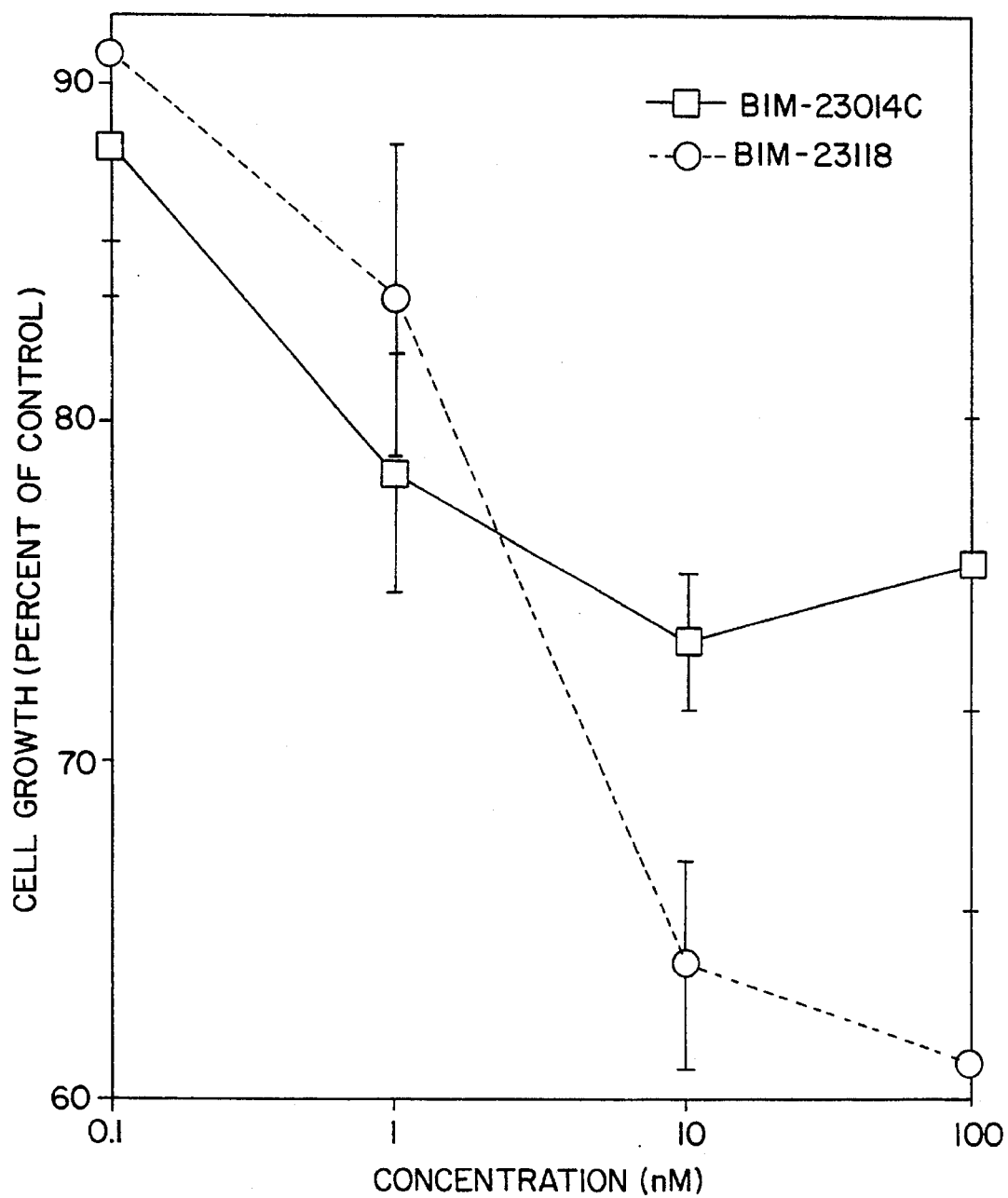
FIG. 1 is a graph of two growth curves of AR42J cells in the presence of different somatostatin derivatives.

In general, peptide derivatives of the invention contain two separate components: 1) a biologically active peptide; and, 2) at least one substituent having the structure of Compounds I, II, and III. Peptide derivatives made according to the methods described herein include the following compounds.

Compound I-Based Derivatives

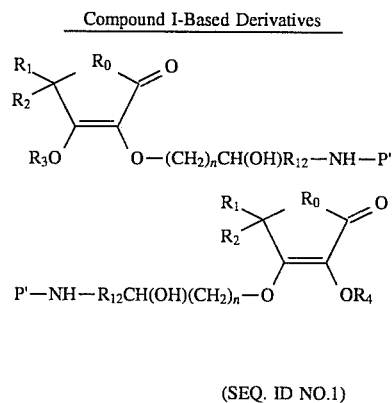

-continued
Compound I-Based Derivatives

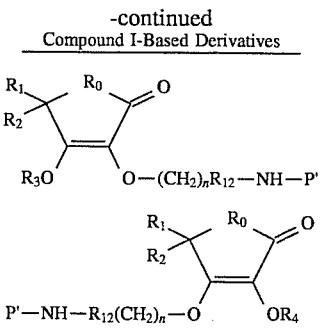

wherein $R_0$, $R_1$, $R_2$, $R_3$, $R_4$, $R_{12}$, and n are as defined herein, and NH-P' is the biologically active peptide moiety. In these embodiments, the NH group is located on the N-terminal end or side chain of the peptide and P' represents the remainder of the peptide.

Compound II-based Derivatives

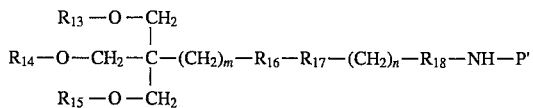

wherein $R_{13}$, $R_{14}$, $R_{15}$, $R_{16}$, $R_{17}$, $R_{18}$, m, n, and NH-P' are as defined herein.

Compound III-Based Derivatives

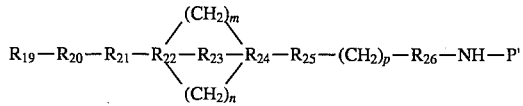

wherein $R_{19}$, $R_{20}$, $R_{21}$, $R_{22}$, $R_{23}$, $R_{24}$, $R_{25}$, $R_{26}$, m, n, p, and NH-P' are as defined herein.

In addition to the structures shown above, compounds made according to the invention include peptide derivatives containing two or more substituents attached to one peptide moiety. These embodiments of the invention are derivatives of biologically active peptides which have more than one free amino group, e.g., a lysine residue.

The invention also provides dimeric peptide derivatives containing two peptide moieties bound to a single substituent, e.g., two Bradykinin analogs bound to a substituent of Compound V.

The peptide derivatives of the invention are derivatives of biologically active peptides selected from the following group: somatostatin, bombesin, calcitonin, calcitonin gene related peptide (CGRP), amylin, parathyroid hormone (PTH), gastrin releasing peptide (GRP), melanocyte stimulating hormone (MSH), adrenocorticotrophic hormone (ACTH), parathyroid related peptide (PTHrP), luteinizing hormone-releasing hormone (LHRH), growth hormone releasing factor (GRF), growth hormone releasing peptide (GHRP), cholecystokinin (CCK), glucagon, bradykinin, glucagon-like peptide (GLP), gastrin, enkephalin, neuromedins, endothelin, substance P, neuropeptide Y (NPY), peptide YY (PYY), vasoactive intestinal peptide (VIP), guanylin, pituitary adenylate cyclase activating polypeptide (PACAP), beta-cell tropin, adrenomedulin, or derivatives, fragments, or analogs of any of the foregoing.

In especially preferred embodiments, the peptide moiety is somatostatin or a derivative, fragment, or analog of somatostatin. Somatostatin analogs which can be used in accordance with the present invention include, but are not limited to the following compounds:

H-D-β-Nal-Cys-Tyr-D-Trp-Lys-Thr-Cys-Thr-NH₂ (SEQ ID NO.4);

H-D-Phe-Cys-Phe-D-Trp-Lys-Thr-Cys-β-Nal-NH₂ (SEQ ID NO.5);

H-D-Phe-Cys-Tyr-D-Trp-Lys-Thr-Cys-β-Nal-NH₂ (SEQ ID NO.6);

H-D-β-Nal-Cys-Phe-D-Trp-Lys-Thr-Cys-Thr-NH₂ (SEQ ID NO.7);

H-D-Phe-Cys-Tyr-D-Trp-Lys-Thr-Pen-Thr-NH₂ (SEQ ID NO.8);

H-D-Phe-Cys-Phe-D-Trp-Lys-Thr-Pen-Thr-NH₂; (SEQ ID NO.9)

H-D-Phe-Cys-Tyr-D-Trp-Lys-Thr-Pen-Thr; (SEQ ID NO.8)

H-D-Phe-Cys-Phe-D-Trp-Lys-Thr-Pen-Thr; (SEQ ID NO.9)

H-Gly-Pen-Phe-D-Trp-Lys-Thr-Cys-Thr; (SEQ ID NO.10)

H-Phe-Pen-Tyr-D-Trp-Lys-Thr-Cys-Thr; (SEQ ID NO.11)

H-Phe-Pen-Phe-D-Trp-Lys-Thr-Pen-Thr; (SEQ ID NO.12)

H-D-Phe-Cys-Phe-D-Trp-Lys-Thr-Cys-Thr-ol; (SEQ ID NO.13)

H-D-Phe-Cys-Phe-D-Trp-Lys-Thr-Cys-Thr-NH₂; (SEQ ID NO.13)

H-D-Trp-Cys-Tyr-D-Trp-Lys-Val-Cys-Thr-NH₂; (SEQ ID NO.14)

H-D-Trp-Cys-Phe-D-Trp-Lys-Thr-Cys-Thr-NH₂; (SEQ ID NO.15)

H-D-Phe-Cys-Tyr-D-Trp-Lys-Val-Cys-Thr-NH₂; (SEQ ID NO.16)

H-D-Phe-Cys-Tyr-D-Trp-Lys-Val-Cys-Trp-NH₂; (SEQ ID NO.17)

H-D-Phe-Cys-Tyr-D-Trp-Lys-Val-Cys-Thr-NH₂; (SEQ ID NO.16)

Ac-D-Phe-Lys*-Tyr-D-Trp-Lys-Val-Asp-Thr-NH₂; (SEQ ID NO.18)

Ac-hArg(Et)₂-Gly-Cys-Phe-D-Trp-Lys-Thr-Cys-Thr-NH₂; (SEQ ID NO.19)

Ac-D-hArg(Et)₂-Gly-Cys-Phe-D-Trp-Lys-Thr-Cys-Thr-NH₂; (SEQ ID NO.20)

Ac-D-hArg(Bu)-Gly-Cys-Phe-D-Trp-Lys-Thr-Cys-Thr-NH₂; (SEQ ID NO.21)

Ac-D-hArg(Et)₂-Cys-Phe-D-Trp-Lys-Thr-Cys-Thr-NH₂; (SEQ ID NO.22)

Ac-L-hArg(Et)₂-Cys-Phe-D-Trp-Lys-Thr-Cys-Thr-NH₂; (SEQ ID NO.23)

Ac-D-hArg(CH₂CF₃)₂-Cys-Phe-D-Trp-Lys-Thr-Cys-Thr-NH₂; (SEQ ID NO.24)

Ac-D-hArg(CH₂CF₃)₂-Gly-Cys-Phe-D-Trp-Lys-Thr-Cys-Thr-NH₂; (SEQ ID NO.25)

Ac-D-hArg(CH₂CF₃)₂-Gly-Cys-Phe-D-Trp-Lys-Thr-Cys-Phe-NH₂; (SEQ ID NO.26)

Ac-D-hArg(CH₂CF₃)₂-Gly-Cys-Phe-D-Trp-Lys-Thr-Cys-Thr-NHEt; (SEQ ID NO.25)

Ac-L-hArg(CH₂—CF₃)₂-Gly-Cys-Phe-D-Trp-Lys-Thr-Cys-Thr-NH₂; (SEQ ID NO.27)

Ac-D-hArg(CH₂CF₃)₂-Gly-Cys-Phe-D-Trp-Lys(Me)-Thr-Cys-Thr-NH₂; (SEQ ID NO.28)

Ac-D-hArg(CH₂CF₃)₂-Gly-Cys-Phe-D-Trp-Lys (Me)-Thr-Cys-Thr-NHEt; (SEQ ID NO.28)

Ac-hArg(CH₃, hexyl)-Gly-Cys-Phe-D-Trp-Lys-Thr-Cys-Thr-NH₂; (SEQ ID NO.29)

H-hArg(hexyl₂)-Gly-Cys-Phe-D-Trp-Lys-Thr-Cys-Thr-NH₂; (SEQ ID NO.30)

Ac-D-hArg(Et)₂-Gly-Cys-Phe-D-Trp-Lys-Thr-Cys-Thr-NHEt

Ac-D-hArg(Et)₂-Gly-Cys-Phe-D-Trp-Lys-Thr-Cys-Phe-NH₂; (SEQ ID NO.32)

Propionyl-D-hArg(Et)₂-Gly-Cys-Phe-D-Trp-Lys(iPr)-Thr-Cys-Thr-NH₂; (SEQ ID NO.33)

Ac-D-β-Nal-Gly-Cys-Phe-D-Trp-Lys-Thr-Cys-Gly-hArg(Et)₂—NH₂; (SEQ ID NO.34)

Ac-D-Lys(iPr)-Gly-Cys-Phe-D-Trp-Lys-Thr-Cys-Thr-NH₂; (SEQ ID NO.35)

Ac-D-hArg(CH₂CF₃)₂-D-hArg(CH₂CF₃)₂-Gly-Cys-Phe-D-Trp-Lys-Thr-Cys-Thr-NH₂; (SEQ ID NO. 36)

Ac-D-hArg(CH$_2$CF$_3$)$_2$-D-hArg(CH$_2$CF$_3$)$_2$-Gly-Cys-Phe-D-Trp-Lys-Thr-Cys-Phe-NH$_2$; (SEQ ID NO. 37)

Ac-D-hArg(Et)$_2$-D-hArg(Et)$_2$-Gly-Cys-Phe-D-Trp-Lys-Thr-Cys-Thr-NH$_2$; (SEQ ID NO.38)

Ac-Cys-Lys-Asn-4-Cl-Phe-Phe-D-Trp-Lys-Thr-Phe-Thr-Ser-D-Cys-NH$_2$; (SEQ ID NO.39)

Bmp-Tyr-D-Trp-Lys-Val-Cys-Thr-NH$_2$; (SEQ ID NO.40)

Bmp-Tyr-D-Trp-Lys-Val-Cys-Phe-NH$_2$; (SEQ ID NO.41)

Bmp-Tyr-D-Trp-Lys-Val-Cys-p-Cl-Phe-NH$_2$; (SEQ ID NO.42)

Bmp-Tyr-D-Trp-Lys-Val-Cys-β-Nal-NH$_2$; (SEQ ID NO.43)

H-D-β-Nal-Cys-Tyr-D-Trp-Lys-Val-Cys-Thr-NH$_2$; (SEQ ID NO.44)

H-D-Phe-Cys-Tyr-D-Trp-Lys-Abu-Cys-Thr-NH$_2$; (SEQ ID NO.45)

H-D-Phe-Cys-Tyr-D-Trp-Lys-Abu-Cys-β-Nal-NH$_2$; (SEQ ID NO.46)

H-pentafluoro-D-Phe-Cys-Tyr-D-Trp-Lys-Val-Cys-Thr-NH$_2$;

Ac-D-β-Nal-Cys-pentafluoro-Phe-D-Trp-Lys-Val-Cys-Thr-NH$_2$; (SEQ ID NO.48)

H-D-β-Nal-Cys-Tyr-D-Trp-Lys-Val-Cys-β-Nal-NH$_2$; (SEQ ID NO.49)

H-D-Phe-Cys-Tyr-D-Trp-Lys-Val-Cys-β-Nal-NH$_2$; (SEQ ID NO.50)

H-D-β-Nal-Cys-Tyr-D-Trp-Lys-Abu-Cys-Thr-NH$_2$; (SEQ ID NO.51)

H-D-p-Cl-Phe-Cys-Tyr-D-Trp-Lys-Abu-Cys-Thr-NH$_2$; (SEQ ID NO.52)

Ac-D-p-Cl-Phe-Cys-Tyr-D-Trp-Lys-Abu-Cys-Thr-NH$_2$; (SEQ ID NO.53)

H-D-Phe-Cys-β-Nal-D-Trp-Lys-Val-Cys-Thr-NH$_2$; (SEQ ID NO.54)

H-D-Phe-Cys-Tyr-D-Trp-Lys-Cys-Thr-NH$_2$; (SEQ ID NO.55)

cyclo (Pro-Phe-D-Trp-N-Me-Lys-Thr-Phe); (SEQ ID NO.55)

cyclo (Pro-Phe-D-Trp-N-Me-Lys-Thr-Phe); (SEQ ID NO.56)

cyclo (Pro-Phe-D-Trp-Lys-Thr-N-Me-Phe); (SEQ ID NO.57)

cyclo (N-Me-Ala-Tyr-D-Trp-Lys-Thr-Phe); (SEQ ID NO.58)

cyclo (Pro-Tyr-D-Trp-Lys-Thr-Phe); (SEQ ID NO.59)

cyclo (Pro-Phe-D-Trp-Lys-Thr-Phe); (SEQ ID NO.60)

cyclo (Pro-Phe-L-Trp-Lys-Thr-Phe); (SEQ ID NO.61)

cyclo (Pro-Phe-D-Trp(F)-Lys-Thr-Phe); (SEQ ID NO.62)

cyclo (Pro-Phe-Trp(F)-Lys-Thr-Phe); (SEQ ID NO.63)

cyclo (Pro-Phe-D-Trp-Lys-Ser-Phe); (SEQ ID NO.64)

cyclo (Pro-Phe-D-Trp-Lys-Thr-p-Cl-Phe); (SEQ ID NO.65)

cyclo (D-Ala-N-Me-D-Phe-D-Thr-D-Lys-Trp-D-Phe); (SEQ ID NO.66)

cyclo (D-Ala-N-Me-D-Phe-D-Val-Lys -D-Trp-D-Phe); (SEQ ID NO.67)

cyclo (D-Ala-N-Me-D-Phe-D-Thr-Lys-D-Trp-D-Phe);

cyclo (D-Abu-N-Me-D-Phe-D-Val-Lys-D-Trp-D-Tyr); (SEQ ID NO.68)

cyclo (N-Me-Ala-Tyr-D-Trp-Lys-Val-Phe); (SEQ ID NO.69)

cyclo (Pro-Tyr-D-Trp-4-Amphe-Thr-Phe); (SEQ ID NO.70)

cyclo (Pro-Phe-D-Trp-4-Amphe-Thr-Phe); (SEQ ID NO.71)

cyclo (N-Me-Ala-Tyr-D-Trp-4-Amphe-Thr-Phe); (SEQ ID NO.72)

cyclo (Asn-Phe-Phe-D-Trp-Lys-Thr-Phe-Gaba); (SEQ ID NO.73)

cyclo (Asn-Phe-Phe-D-Trp-Lys-Thr-Phe-Gaba-Gaba); (SEQ ID NO.73)

cyclo (Asn-Phe-D-Trp-Lys -Thr-Phe); (SEQ ID NO.74)

cyclo (Asn-Phe-Phe-D-Trp-Lys-Thr-Phe-NH(CH$_2$)$_4$CO); (SEQ ID NO.75)

cyclo (Asn-Phe-Phe-D-Trp-Lys-Thr-Phe-β-Ala); (SEQ ID NO.75)

cyclo (Asn-Phe-Phe-D-Trp-Lys-Thr-Phe-D-Glu)-OH; (SEQ ID NO.76)

cyclo (Phe-Phe-D-Trp-Lys-Thr-Phe); (SEQ ID NO.77)

cyclo (Phe-Phe-D-Trp-Lys-Thr-Phe-Gly); (SEQ ID NO.78)

cyclo (Phe-Phe-D-Trp-Lys-Thr-Phe-Gaba); (SEQ ID NO.77)

cyclo (Asn-Phe-Phe-D-Trp-Lys-Thr-Phe-Gly); (SEQ ID NO.79)

cyclo (Asn-Phe-Phe-D-Trp(F)-Lys-Thr-Phe-Gaba); (SEQ ID NO.80)

cyclo (Asn-Phe-Phe-D-Trp(NO$_2$)-Lys-Thr-Phe-Gaba); (SEQ ID NO.81)

cyclo (Asn-Phe-Phe-Trp(Br)-Lys-Thr-Phe-Gaba); (SEQ ID NO.82)

cyclo (Asn-Phe-Phe-D-Trp-Lys-Thr-Phe(I)-Gaba); (SEQ ID NO.83)

cyclo (Asn-Phe-Phe-D-Trp-Lys-Thr-Tyr(But)-Gaba); (SEQ ID NO.84)

cyclo (Bmp-Lys-Asn-Phe-Phe-D-Trp-Lys-Thr-Phe-Thr-Pro-Cys)-OH; (SEQ ID NO.85)

cyclo (Bmp-Lys-Asn-Phe-Phe-D-Trp-Lys-Thr-Phe-Thr-Pro-Cys)-OH; (SEQ ID NO.85)

cyclo (Bmp-Lys-Asn-Phe-Phe-D-Trp-Lys-Thr-Phe-Thr-Tpo-Cys)-OH; (SEQ ID NO.86)

cyclo (Bmp-Lys-Asn-Phe-Phe-D-Trp-Lys-Thr-Phe-Thr-MeLeu-Cys)-OH; (SEQ ID NO.87)

cyclo (Phe-Phe-D-Trp-Lys-Thr-Phe-Phe-Gaba); (SEQ ID NO.88)

cyclo (Phe-Phe-D-Trp-Lys-Thr-Phe-D-Phe-Gaba); (SEQ ID NO.89)

cyclo (Phe-Phe-D-Trp(5F)-Lys-Thr-Phe-Phe-Gaba); (SEQ ID NO.90)

cyclo (Asn-Phe-Phe-D-Trp-Lys(Ac)-Thr-Phe-NH-(CH$_2$)$_3$-CO); (SEQ ID NO.91)

cyclo (Lys-Phe-Phe-D-Trp-Lys-Thr-Phe-Gaba); (SEQ ID NO.92)

cyclo (Lys-Phe-Phe-D-Trp-Lys-Thr-Phe-Gaba); (SEQ ID NO.92) and cyclo (Orn-Phe-Phe-D-Trp-Lys-Thr-Phe-Gaba); (SEQ ID NO.95)

where Lys* indicates an amide bridge formed between Lys* and Asp.

The peptide compounds listed above are described in the following references, each of which is incorporated herein by reference:

EP Application No. P5 164 EU; Van Binst, G. et al. Peptide Research 5:8 (1992); Horvath, A. et al. Abstract, "Conformations of Somatostatin Analogs Having Anti-tumor Activity", 22nd European Peptide Symposium, Sep. 13–19, 1992, Interlaken, Switzerland; PCT Application WO 91/09056 (1991); EP Application 0 363 589 A2 (1990); EP Application 0 203 031 A2 (1986); U.S. Pat. Nos. 4,904,642; 4,871,717; 4,853,371; 4,725,577; 4,684,620; 4,650,787; 4,603,120; 4,585,755; 4,522,813; 4,486,415; 4,485,101; 4,435,385; 4,395,403; 4,369,179; 4,360,516; 4,358,439; 4,328,214; 4,316,890; 4,310,518; 4,291,022; 4,238,481; 4,235,886; 4,224,190; 4,211,693; 4,190,648; 4,146,612; and 4,133,782.

In the somatostatin analogs listed above, each amino acid residue has the structure of NH—C(R)H—CO—, in which R is the side chain; lines between amino acid residues represent peptide bonds which join the amino acids. When the amino acid residue is optically active, it is the L-form configuration that is intended unless the D-form is expressly designated. When two Cys residues are present in the peptide, a disulfide bridge is formed between the two moieties. This bond, however, is not shown in the listed residues.

Additionally preferred somatostatin analogs of the invention are of the following formula:

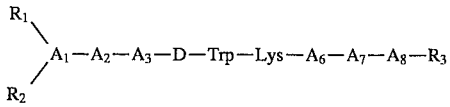

wherein $A_1$ is a D- or L-isomer of β-Nal, Trp, β-pyridyl-Ala, Phe, substituted Phe, or deleted; and each $A_2$ and $A_7$, independently, is Cys, Asp, or Lys. These moieties are covalently linked to each other via a disulfide bridge or an amide bridge. In addition, $A_3$ is β-Nal, Phe, or o-, m-, or p-substituted X-Phe where X is a halogen, OH, $NH_2$, $NO_2$ or $C_{1-3}$ alkyl; $A_6$ is Val, Thr, Ser, Ala, Phe, β-Nal, Abu, Ile, Nle, or Nva; and $A_8$ is Phe, Thr, Tyr, Trp, Ser, β-Nal, an alcohol group, or deleted; each $R_1$ and $R_2$, independently, is H, lower acyl or lower alkyl; and $R_3$ is OH, $NH_2$, or deleted. Preferably, when one of $A_2$ and $A_7$ is Cys, the other is also Cys; when $A_8$ is an alpha-amino alcohol, $R_3$ is deleted; and when neither of $A_2$ and $A_7$ is Cys, $A_2$ is different from $A_7$.

Especially preferred somatostatin analogs of this embodiment are:

Me-D-Phe-Cys-Tyr-Tyr-D-Trp-Lys-Val-Cys-Thr-NH₂; (SEQ ID NO.94)

H-D-Nal-Cys-Tyr-D-Trp-Lys-Thr-Cys-Nal-NH₂; (SEQ ID NO.95)

H-D-Nal-Cys-Tyr-D-Trp-Lys-Thr-Cys-Thr-NH₂; (SEQ ID NO.96)

H-D-Phe-Cys-Tyr-D-Trp-Lys-Abu-Cys-Thr-NH₂; (SEQ ID NO.97)

H-D-Phe-Cys-Tyr-D-Trp-Lys-Thr-Cys-Nal-NH₂; (SEQ ID NO.98) and

H-D-Phe-Cys-Tyr-D-Trp-Lys-Thr-Cys-Thr-ol. (SEQ ID NO.99)

In other embodiments, linear somatostatin analogs of the invention have the following structure:

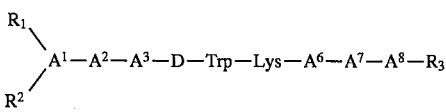

wherein $A^1$ is a D- or L- isomer of Ala, Leu, Ile, Val, Nle, Thr, Ser, β-Nal, β-pyridyl-Ala, Trp, Phe, 2,4-dichloro-Phe, pentafluoro-Phe, p-X-Phe, or o-X-Phe, wherein X is $CH_3$, Cl, Br, F, OH, $OCH_3$ or $NO_2$;

$A^2$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;

$A^3$ is pyridyl-Ala, Trp, Phe, β-Nal, 2,4-dichloro-Phe, pentafluoro-Phe, o-X-Phe, or p-X-Phe, wherein X is $CH_3$, Cl, Br, F, OH, $OCH_3$ or $NO_2$;

$A^6$ is Val, Ala, Leu, Ile, Nle, Thr, Abu, or Ser;

$A^7$ is Ala, Leu, Ile, Val, Nle, Phe, β-Nal, pyridyl-Ala, Trp, 2,4-dichloro-Phe, pentafluoro-Phe, o-X-Phe, or p-X-Phe, wherein X is $CH_3$, Cl, Br, F, OH, $OCH_3$ or $NO_2$;

$A^8$ is a D- or L-isomer of Ala, Leu, Ile, Val, Nle, Thr, Ser, Phe, β-Nal, pyridyl-Ala, Trp, 2,4-dichloro-Phe, pentafluoro-Phe, p-X-Phe, or o-X-Phe, wherein X is $CH_3$, Cl, Br, F, OH, $OCH_3$ or $NO_2$, or an alcohol thereof; and each $R_1$ and $R_2$, independently, is H, lower acyl or lower alkyl; and $R_3$ is OH, $NH_2$, or deleted. Preferably, at least one of $A^1$ and $A^8$ and one of $A^2$ and $A^7$ must be an aromatic amino acid; and when $A^8$ is an alcohol, $R_3$ is deleted. Additionally, $A^1$, $A^2$, $A^7$ and $A^8$ cannot all be aromatic amino acids. Particularly preferred analogs of this aspect of the invention include:

H-D-Phe-p-chloro-Phe-Tyr-D-Trp-Lys-Thr-Phe-Thr-NH₂; (SEQ ID NO.100)

H-D-Phe-p-NO₂-Phe-Tyr-D-Trp-Lys-Val-Phe-Thr-NH₂; (SEQ ID NO.101)

H-D-Nal-p-chloro-Phe-Tyr-D-Trp-Lys-Val-Phe-Thr-NH₂; (SEQ ID NO.102)

H-D-Phe-Phe-Phe-D-Trp-Lys-Thr-Phe-Thr-NH₂; (SEQ ID NO.103)

H-D-Phe-Phe-Tyr-D-Trp-Lys-Val-Phe-Thr-NH₂; (SEQ ID NO.104)

H-D-Phe-p-chloro-Phe-Tyr-D-Trp-Lys-Val-Phe-Thr-NH₂; (SEQ ID NO.105) and

H-D-Phe-Ala-Tyr-D-Trp-Lys-Val-Ala-D-β-Nal-NH₂. (SEQ ID NO.106)

In still other preferred embodiments, the peptide moiety is bombesin or a derivative, fragment, or analog of bombesin. Bombesin analogs which can be used to practice the present invention include, but are not limited to, Neuromedin C, Neuromedin B, litorin, and gastrin-releasing peptide (GRP), which has the following amino acid sequence:

H—Ala—Pro—Val—Ser—Val—Gly—Gly—Gly—    (SEQ. ID NO. 108)
    Thr—Val—
—Leu—Ala—Lys—Met—Tyr—Pro—Arg—Gly—
                Asn—His—
    —Trp—Ala—Val—Gly—His—Leu—Met—NH₂

Other bombesin analogs which may be used in the present invention include compounds described in the following references, the contents of which are incorporated herein by reference:

Coy et al. Peptides, Proceedings of the Eleventh Amer. Peptide Symposium, Ed. by Rivier et al. ESCOM, pp. 65–67 (1990); Wang et al. J. Biol. Chem. 265:15695 (1990); Mahmoud et al. Cancer Research 51:1798 (1991); Wang et al. Biochemistry 29:616 (1990); Heimbrook et al., "Synthetic Peptides: Approaches to Biological Problems", UCLA Symposium on Mol. and Cell Biol New Series, Vol. 86, ed. Tam and Kaiser; Martinez et al., J. Med. Chem. 28:1874 (1985); Gargosky et al., Biochem. J. 247:427 (1987); Dubreuil et al., Drug Design and Delivery, Vol 2:49, Harwood Academic Publishers, GB (1987); Heikkila et al., J. Biol. Chem. 262:16456 (1987); Caranikas et al., J. Med. Chem. 25:1313 (1982); Saeed et al., Peptides 10:597 (1989); Rosell et al., Trends in Pharmacological Sciences 3:211

(1982); Lundberg et al., Proc. Nat. Aca. Sci. 80:1120, (1983); Engberg et al., Nature 293:222 (1984); Mizrahi et al., Euro. J. Pharma. 82:101 (1982); Leander et al., Nature 294:467 (1981); Woll et al., Biochem. Biophys. Res. Comm. 155:359 (1988); Rivier et al., Biochem. 17:1766 (1978) Cuttitta et al., Cancer Surveys 4:707 (1985); Aumelas et al., Int. J. Peptide Res. 30:596 (1987); Szepeshazi. et al., Cancer Research 51:5980 (1991); Jensen, et al. Trends Pharmacol. Sci. 12:13 (1991); U.S. Pat. Nos. 5,028,692; 4,943,561; 4,207,311; 5,068,222; 5,081,107; 5,084,555; EP Application Nos. 0 315 367 A2 (1989); 0 434 979 A1 (1991); 0 468 497 A2 (1992); 0 313 158 A2 (1989); 0 339 193 A1 (1989); PCT Applications Nos. WO 90/01037 (1990); 90/02545 (1992); and UK Application GB 1 231 051 A (1990).

The peptides of the invention can be provided in the form of pharmaceutically acceptable salts. Examples of preferred salts are those with therapeutically acceptable organic acids, e.g., acetic, lactic, maleic, citric, malic, ascorbic, succinic, benzoic, salicylic, methanesulfonic, toluenesulfonic, or pamoic acid, as well as polymeric acids such as tannic acid or carboxymethyl cellulose, and salts with inorganic acids such as hydrohalic acids, including hydrochloric acid, sulfuric acid, and phosphoric acid.

Synthesis of Compounds

The syntheses of Compounds I, II and III are now described.

The following abbreviations are used in describing syntheses of compounds according to the present invention:

Nal: naphthylalanine (1 or 2)

Abu: alpha-aminobutyric acid

D: dextrorotatory

L: levorotatory

HOAC: acetic acid

BOP: benzotriazol-1-yloxytris(dimethylamino) phosphonium hexafluoro-phosphate

BOC: tert-butyloxycarbonyl

DCC: dicyclohexyl carbodiimide

EDC: 1-(3-dimethylaminopropyl)-3-ethylcarbodiimide

DEPC: diethylcyanophosphonate

DMF: dimethylformamide $CH_2CL_2$: dichloromethane

MeOH: methanol

EtOH: ethanol

DIEA: N,N-diisopropylethylamine

HOBT: 1-hydroxybenzotriazole

HBTU: O-Benzotriazol-1-yl,N,N,N',N'-tetramethyluronium hexafluorophosphate

THF: Tetrahydrofuran

TFA: Trifluoroacetic Acid

Starting materials and intermediates for Compounds I, II, and II are commercially available. Alternatively, the starting materials can be easily prepared by methods which are well known and included in the literature. For example, the chemistry of ascorbic acid-related derivatives can be found in *J. Chem. Soc.*, Perkin Trans. 1:1220 (1974); *Carbohyd. Res.*, 67:127 (1978); *Yakugaku Zasshi*, 86:376 (1966); U.S. Pat. No. 4,552,888; *J. Med. Chem.*, 31:793 (1988); ibid. 34:2152 (1991); and, 35:1618 (1992), the contents of which are incorporated herein by reference. The chemistry for tris-related derivatives can be found in *Arch. Biochem. Biophy*, 96, 653 (1962), *Biochem.*, 5 467 (1966), the contents of which are also incorporated herein by reference.

Synthesis of Peptide Derivatives

In a general sense, the coupling of Compounds I, II, or III to an appropriate free amino group of a protected amino acid or peptide can be achieved according to well-known methods employed for peptide synthesis (e.g., DCC, DCC-HOBT, DIC-HOBT PPA, EDC-HOBT, DEPT, BOP, HBTU) using a base (e.g. DIEA) in an inert solvent (e.g. DMF, THF or $CH_2Cl_2$ ethyl acetate or combination thereof). Deblocking of protected groups may also be carried out by well-known methods (e.g., removal of the group by the addition of acid or base, TFA, dioxan-HCl, ammonia, NaOMe, piperidine). In most cases, the reaction temperature should range from $-30°$ C. to room temperature.

In general, the first step of the synthesis involves the reaction between an epoxide and a free amino group of a protected amino acid or peptide; complexation and deprotection can be achieved utilizing well-known methods, such as those described in McManus, et al., *Synth. Communications* 3, 177 (1973), the contents of which are incorporated herein by reference. Following synthesis, purification of the intermediates and products can be achieved by conventional methods such as chromatography or HPLC. The identification of the compounds may be determined by conventional techniques such as NMR, amino acid analysis, and mass spectrometry.

The following Examples illustrate the preferred methods for forming the compounds of the invention.

EXAMPLE 1—

Synthesis of Somatostatin Derivatives

The following somatostatin derivative, also referred to herein as BIM-23118, was synthesized in accordance with the invention:

(SEQ. ID NO. 108)

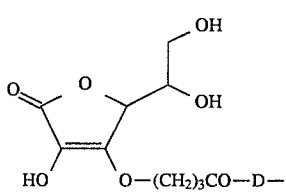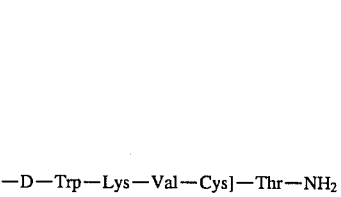

EXAMPLE 1.1—

3-0-(Benzyloxycarbonylmethyl)-2,5,6-triacetyl-ascorbic acid

Acetic anhydride (6 ml) was added dropwise to a solution of 3-0- (benzyloxycarbonylmethyl) -ascorbic acid (2.2 g) in pyridine (30 ml) the mixture was then stirred overnight at room temperature. Pyridine was evaporated under reduced pressure leaving a residue which was then partitioned between ethyl acetate and 1N HCl. The ethyl acetate layer was washed with 1N HCl, and then water. After drying ($MgSO_4$), the ethyl acetate was evaporated under reduced pressure; traces of pyridine and acetic anhydride which still remained were removed by multiple co-evaporations with toluene. The resulting 3-0-(Benzyloxycarbonylmethyl)- 2,5, 6-triacetyl-ascorbic acid was dried under vacuum to yield a viscous gel which remained in the residue (2.4 g). TLC (silica gel: $CHCl_3$/acetone [9:1], Rf=0.52).

EXAMPLE 1.2—

3-0-(carboxymethyl)-2,5,6-triacetyl-ascorbic acid

A slurry of Pd-C (100 mg) in water (2 ml) was added to a solution of 3-0-(benzyloxycarbonylmethyl)-2,5,6-triacetyl-ascorbic acid (2.4 g) in ethanol (30 ml), and the suspension was shaken under hydrogen (17 psi) for six hours. The catalyst was then removed by filtration through a celite pad and the filtrate evaporated under reduced pressure to yield 3-0-(carboxymethyl)-2,5,6-triacetyl-ascorbic acid. TLC (silica gel: $CHCl_3/MeOH/HOAc$ [9:1:0.1], Rf=0.2).

EXAMPLE 1.3—

5,6-0-Isopropylideneascorbic acid

Acetylchloride (0.67 ml) was added to a rapidly stirred suspension of ascorbic acid (8.0 g) in acetone (80 ml) and the mixture was stirred at room temperature overnight. The precipitate was collected by filtration, washed with ethyl acetate, and dried at reduced pressure to afford 8.29 g of 5,6-0-Isopropylideneascorbic acid as a colorless solid. TLC (silica gel: $CHCl_3/MeOH/HOAC$ [3:1:0.1], Rf=0.54).

EXAMPLE 1.4—

3-0-(Ethoxycarbonylpropyl)-5,6-isopropylidene-ascorbic acid

A solution of 5,6-isopropylidene ascorbic acid (2.0 g) in 10 ml DMF was added dropwise to a suspension of NaH (0.44 g of 50% mineral oil NaH dispersion washed with hexane several times) in 5 ml DMF. After gas evolution ceased, a solution of 1.43 ml ethyl 4-bromobutyrate in 5 ml DMF was added dropwise and the mixture was stirred at room temperature overnight. Solvent was evaporated at reduced pressure and the resultant residue was chromatographed on silica gel (55 g) using $CHCl_3/MeOH$ (19:1) as an eluant. Appropriate fractions were pooled and solvents removed at reduced pressure to yield a viscous residue containing 3-0-(Ethoxycarbonylpropyl)- 5,6-isopropylidene-ascorbic acid (1.1 g).

EXAMPLE 1.5—

3-0-(carboxypropyl)-5,6-isopropylidene ascorbic acid 4.6 ml of 2N-NaOH was added to a solution of 3-0-(ethyoxycarbonylpropyl)- 5,6-isopropylidene-ascorbic acid (1.02 g) in 15 ml EtOH. After one hour, most of the ethanol was removed at reduced pressure and the residue was diluted with water (10 ml), and acidified with dil-HCL (pH 3). The solution was then saturated with NaCl and extracted several times with ethyl acetate; the pooled extracts were then dried using $MgSO_4$. Solvent was evaporated at reduced pressure to yield a viscous residue containing 3-0-(carboxypropyl)-5,6-isopropylidene ascorbic acid (0.84 g). TLC: (Silica gel: $CHCl_3/MeOH/HOAC$ [5:1:0.1], Rf=0.55).

EXAMPLE 1.6—

D-Nal-c[Cys-Tyr-D-Trp-Lys(BOC)-Val-Cys]-Thr-$NH_2$ (SEQ ID NO.109)

A solution of di-tertbutyl dicarbonate (0.36 g) in 10 ml DMF was added dropwise to a solution of D-Nal-c[Cys-Tyr-D-Trp-Lys-Val-Cys]-Thr-$NH_2$ (SEQ ID NO. 108) acetate (2 g, BIM-23014) in 45 ml DMF. After two hours at room temperature, solvent was removed under reduced pressure to yield a residue which was then chromatographed on silica gel (150 g) using $CHCl_3/MeOH$(9:1) as an eluant. Appropriate fractions were pooled and solvents removed under reduced pressure to yield a residue containing D-Nal-c[Cys-Tyr-D-Trp-Lys(BOC)-Val-Cys] -Thr-$NH_2$ (SEQ ID NO.109) (1.45 g). TLC (silica gel: $CHCl_3/MeOH$ [3:1], Rf=0.52 ).

EXAMPLE 1.7—

(SEQ ID NO. 109)

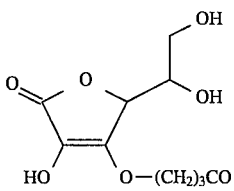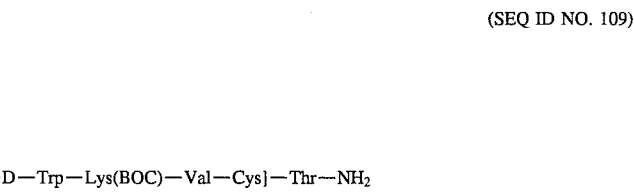

0.2 ml diisopropylethylamine was added to a solution of D-Nal-Cyclo-[Cys-Tyr-D-Trp-Lys(BOC)-Val-Cys]-Thr-$NH_2$ (SEQ ID NO.111) (300 mg), 3-0-(carboxypropyl)-5,6-isopropylidene ascorbic acid (56 mg) and HBTU (113 mg) in 5 ml DMF. The mixture was then stirred at room temperature overnight, and solvent was removed under reduced pressure. The residue was partitioned between a mixture of ethyl acetate/MeOH and a saturated aqueous NaCl solution, and the ethyl acetate layer was washed with saturated aqueous NaCl , then saturated aqueous $NaHCO_3$, and then dried ($MgSO_4$). Solvent was evaporated under reduced pressure, and the residue was subjected to preparative TLC using a $CHCl_3/MeOH$ (8:1) mixture as a developing solvent. The appropriate UV-positive zone was isolated and extracted with $CHCl_3/MeOH$. Solvents were removed at reduced pressure to yield the above-identified product (0.20 g). TLC (silica gel: $CHCl_3/MeOH$[5:1], Rf=0.54).

EXAMPLE 1.8—

Removal of BOC Group

The ascorbic acid derivative containing D-Nal-c[Cys-Tyr-D-Trp-Lys(BOC)-Val-Cys]-Thr-$NH_2$ (SEQ ID NO. 109) (95 mg) shown above was treated with 25% TFA in $CHCl_3$ for 45 min. at room temperature. Volatile substances were removed under reduced pressure to yield a dried residue which was purified using Vydac $C_{18}$ HPLC and $CH_3CN$/ 0.1% aqueous TFA. The final yield was 90 mg (FAB-MS (m/e) 1341).

EXAMPLE 1.9—

Other Embodiments

The following somatostatin derivatives were also synthesized in an analogous manner:

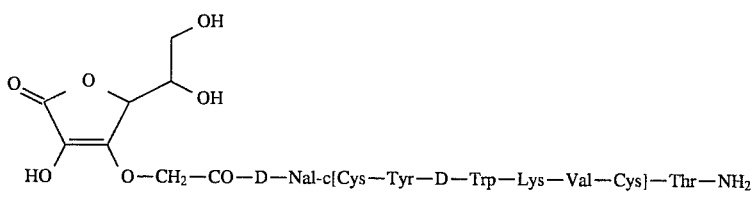

(SEQ ID NO. 110)

BIM-23135

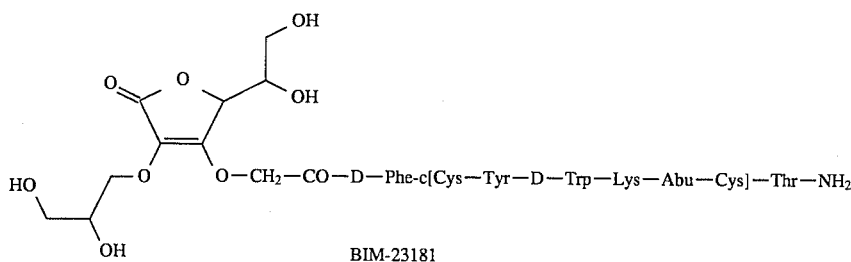

(SEQ ID NO. 112)

BIM-23181

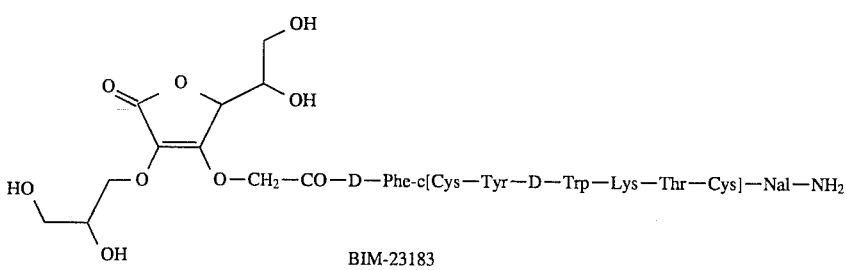

(SEQ ID No. 113)

BIM-23183

EXAMPLE 2—

Synthesis of BIM-23107

The following somatostatin derivative, also referred to as BIM-23107, was synthesized in accordance to the invention.

(AcO-CH$_2$)$_3$-C-NH-CO-(CH$_2$)$_2$-CO-D-Nal-c[Cys-Tyr-D-Trp-Lys-Val-Cys]-Thr-NH$_2$ (SEQ ID NO. 110)

EXAMPLE 2.1—

(AcO-CH$_2$)$_3$-C-NH-CO-(CH$_2$)$_2$-CO-D-Nal-c[Cys-Tyr-D-Trp-Lys(BOC)-Val-Cys]-Thr-NH$_2$ (SEQ ID NO. 109)

0.03 ml DIEA was added to an ice-cooled solution of 2-N-(succinyl)amino-2-(acetoxymethyl)-1,3-propanediol diacetate (83 mg) and HBTU (92 mg) in 2 ml of DMF. After stirring at 0°–5° C. for 30 minutes, a solution of D-Nal-c[Cys-Tyr-D-Trp-Lys(BOC)-Val-Cys]-Thr-NH$_2$ (SEQ ID NO. 109) (100 mg) in 2 ml DMF, containing 0.03 ml DIEA, was added. The mixture was first stirred at 0°–5° C. for one hour and then stirred at room temperature overnight. The solvent was removed at reduced pressure to yield a dried residue which was partitioned between ethyl acetate and aqueous saturated NaCl , and the EtOAc layer washed with aqueous 5% NaHCO, and finally aqueous saturated NaCl; the resulting solution was then dried using MgSO$_4$. The solvent was evaporated under reduced pressure leaving a residue containing (AcO-CH$_2$)$_3$-C-NH-CO-(CH $_2$)$_2$-CO-D-Nal-c[Cys-Tyr-D-Trp-Lys(BOC)-Val-Cys]-Thr-NH $_2$ (SEQ ID NO. 109) (0.14 gm). TLC (Silica Gel: CHCl$_3$/MeOH/HOAc=4:1:0.1, Rf=0.82).

EXAMPLE 2.2—

Removal of BOC group 30 mg of the above-identified compound was treated with 50% TFA in CHCl$_3$ for 45 minutes at room temperature; volatile substances were then removed at reduced pressure to yield a residue. Traces of TFA were co-evaporated with ethanol several times and the residue was titrated with ether and then dried to yield 30 mg of the product (30 mg). TLC (Silica gel: CHCl$_3$/MeOH/HOAc=3:1:1, Rf=0.24).

EXAMPLE 2.3—

Other Embodiments

The following somatostatin derivatives were also synthesized in an analogous manner.

(HO-CH$_2$)$_3$-C-NH-CO-(CH$_2$)$_2$-CO-D-Nal-c[Cys-Tyr-D-Trp-Lys-Val-Cys]-Thr-NH$_2$ (SEQ ID NO. 108)
BIM-23158

(HO-CH$_2$)$_3$-C-NH-CO-(CH$_2$)$_2$-CO-D-Phe-c[Cys-Tyr-D-Trp-Lys-Thr-Cys]-Nal-NH$_2$ (SEQ ID NO. 113)
BIM-23167

(HO-CH$_2$)$_3$-C-NH-CO-(CH$_2$)$_2$-CO-D-Phe-c[Cys-Tyr-D-Trp-Lys-Abu-Cys]-Thr-NH$_2$ (SEQ ID NO.112)
BIM-23173

(HO-CH$_2$)$_3$-C-NH-CH$_2$-CO-D-Phe-c[Cys-Tyr-D-Trp-Lys-Thr-Cys]-Nal-NH $_2$ (SEQ ID NO.113)
BIM-23179

(HO-CH$_2$)$_3$-C-NH-CH$_2$-CO-D-Phe-c[Cys-Tyr-D-Trp-Lys-Abu-Cys]-Thr-NH $_2$ (SEQ ID NO.112)
BIM-23182

EXAMPLE 3—

Synthesis of BIM-23201

The following somatostatin derivative, also referred to as (BIM-23201), was synthesized in accordance with the present invention.

(HO-CH$_2$)$_3$-C-CH$_2$-D-Phe-c[Cys-Tyr-D-Trp-Lys-Thr-Cys]-Nal-NH$_2$ (SEQ ID NO. 113)

EXAMPLE 3.1—

(HO-CH$_2$)$_3$-C-CH$_2$-D-Phe-c[Cys-Tyr-D-Trp-Lys-Thr-Cys]-Nal-NH$_2$ (SEQ ID NO.113)

Two grams of 3 Å molecular sieve followed by NaCNBH$_3$ (36 mg) were added portion-wise in 15 minute increments to a solution of D-Phe-c[Cys Tyr (OBt)-D-Trp-Lys(BOC)-Thr(OBt) Cys] Nal-NH$_2$ (SEQ ID NO. 114) (250 mg) and tris (acetoxymethyl)acetaldehyde (120 mg) obtained by oxidation of triacetyl penta-erythritol with pyridinium dichromate or DMSO/oxalyl chloride/triethylamine) in methanol (10 ml) containing 10% acetic acid. The mixture was then stirred at room temperature for 30 minutes and heated for 4 hours. After filtration, the residue was partitioned between ethyl acetate and water. The ethyl acetate layer was washed with water, then aqueous NaHCO$_3$, and then dried (MgSO$_4$). The solvent was evaporated under reduced pressure to yield a residue (0.4 g) which was then dissolved in methanol (5 ml), treated with a NaOMe/MeOH solution (pH 10), stirred for 1 hour and finally neutralized with 1N HCl to pH 5–6. After evaporation of solvent, the residue was dissolved in 90% aqueous TFA (5 ml) and stirred for 30 minutes. Volatiles were removed at reduced pressure and traces of TFA and water in the resulting residue were removed by co-evaporation with alcohol (2×). The residue was dried, then titrated with ether, and finally purified by HPLC using conditions similar to those described earlier, to yield 41 mg of (HO-CH$_2$)$_3$-C-CH$_2$-D-Phe-c[Cys-Tyr-D-Trp-Lys-Thr-Cys]-Nal-NH$_2$ (SEQ ID NO. 113) as a colorless solid. MS (m/e) 1262.8.

EXAMPLE 3.2—

Other Embodiments

The following somatostatin derivative, also referred to as BIM-23195, was synthesized in an analogous manner.

(Ho-CH$_2$)$_3$C-CH$_2$-D-Phe-C[Cys-Tyr-D-Trp-Lys-Abu-Cys]-Thr-NH$_2$ (SEQ ID NO. 112)
BIM-23195

EXAMPLE 4—

Synthesis of BIM-23197

The following somatostatin derivative, also referred to as BIM-23197, was synthesized in accordance with the invention.

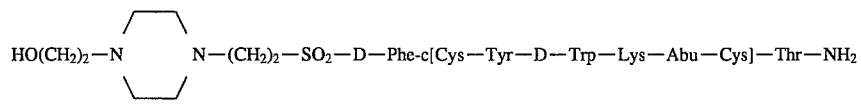

(SEQ ID NO. 112)

EXAMPLE 4.1—

2-Bromoethanesulfonyl Chloride

Na 2-Bromoethanesulfonate (4.0 g) was treated with PCl$_5$ (11.8 g) while cooling in an ice bath. After reaching the liquid phase, the solution was heated at 90°–120° C. for 1.5 hours in oil, cooled to room temperature, poured into 50 g of crushed ice, and then stirred for 15 min. The mixture was extracted with CH$_2$Cl$_2$ (3×30 ml) and combined extracts were washed with H$_2$O (2×), 5% NaHCO$_3$ (2×), and H$_2$O (2×) again. Drying over anhydrous MgSO$_4$ and distillation under reduced pressure gave 2-bromoethanesulfonyl chloride as a colorless liquid (1.95 g, 42°–44° C./1 mm Hg).

EXAMPLE 4.2—

Br-(CH$_2$)$_2$-SO$_2$ -D-Phe-c[Cys-Tyr(tBu)-D-Trp-Lys(Boc)-Abu-Cys]-Thr(tBu)-NH(1-cyclopropyl-1-methyl)-ethyl (SEQ ID NO. 115)

A solution of 2-bromoethane sulfonyl chloride (30 mg) in DMF (1 ml) was added dropwise to a solution of H-D-Phe-c[Cys-Tyr(tBu)-D-Trp-Lys(Boc)-Abu-Cys]-Thr(tBu)-(1-cyclopropyl- 1-methyl)-ethyl (150 mg) and DIEA (55 mg) in DMF (2 ml) under N$_2$ at 0° C. The reaction mixture was stirred at 0°–5° C. for 3 hours; solvent was then removed under reduced pressure. The residue was dissolved in ethyl acetate and washed with 5% citric acid (2×), 5% NaHCO$_3$ (2×) and brine (2×). The solution was then dried over anhydrous MgSO$_4$, filtered, and condensed to dryness under reduced pressure. The product was further purified by a short silica gel column eluted with ethyl acetate. Fractions containing the product were pooled and the solvent was removed under reduced pressure, giving 105 mg of Br-(CH$_2$)$_2$-SO$_2$-D-Phe-c[Cys-Tyr(tBu)-D-Trp-Lys(Boc)-Abu-Cys]-Thr(tBu)-NH(1-cyclopropyl- 1-methyl)-ethyl (SEQ ID NO. 115) as a slightly yellow solid. (Silica gel, CHCl$_3$/MeOH/HOAc (9:1:0.1), Rf=0.36).

EXAMPLE 14.3—

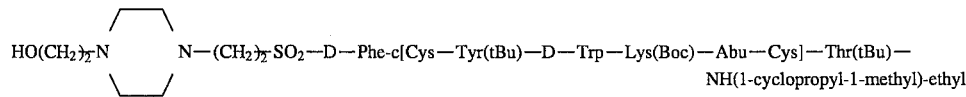

(SEQ ID NO. 115)

A solution of Br-(CH$_2$)$_2$-SO$_2$-D-Phe-c[Cys-Tyr(tBu)-D-Trp-Lys(Boc)-Abu-Cys]-Thr(tBu)-NH(1-cyclopropyl-1-methyl)-ethyl (SEQ ID NO.115) (100 mg) and 2-hydroxyethylpiperazine (55 mg) in 2 ml of 1-propanol was refluxed under N$_2$ for 2.5 hours. The solution was then cooled to room temperature, and the solvent was removed under reduced pressure. The residue was then dissolved in ethyl acetate containing 5% MeOH and washed with brine (3×). Finally, the solution was dried over anhydrous MgSO$_4$, filtered and condensed to dryness under reduced pressure, resulting in 110 mg of the above-identified solid. Without further purification, this compound was used directly in the next step.

EXAMPLE 4.4—

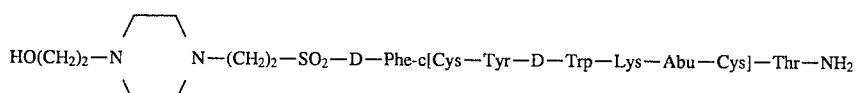

(SEQ ID NO. 112)

110 mg of the protected somatostatin derivative obtained in the previous step was dissolved in 10 ml of 90% TFA aqueous solution, and stirred at room temperature under $N_2$ for one hour. TFA and $H_2O$ were removed under reduced pressure, and the residue was titrated with cold ether (3×10 ml). A slightly yellow solid was obtained; this material was further purified on preparative reverse phase HPLC, eluting with: 1) a $NH_4OAc$ aqueous solution; and, 2) an HOAc aqueous solution. Lyophilization of the pooled fractions containing the above-identified product gave a white solid. (18 mg. ESI-MS, ((m+1)/e) 1252.7).

EXAMPLE 4.5—

Other Embodiments

The following somatostatin derivatives were also synthesized in an analogous manner:

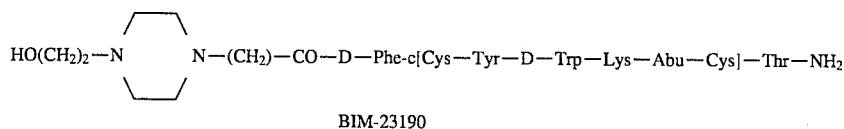

BIM-23190 (SEQ ID NO. 112)

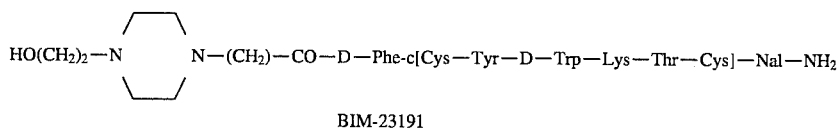

BIM-23191 (SEQ ID NO. 113)

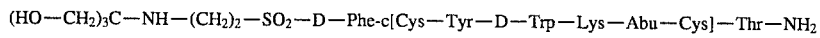

BIM-23196 (SEQ ID NO. 112)

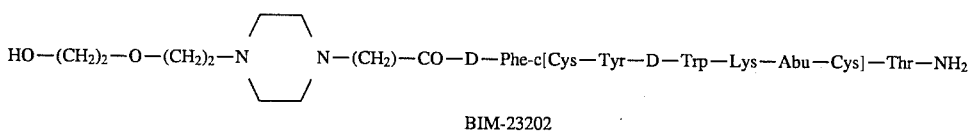

BIM-23202 (SEQ ID NO. 112)

EXAMPLE 5—

Synthesis of Bombesin Derivatives

The following bombesin derivative, also referred to as BIM-26333, was synthesized in an analogous manner as described above:

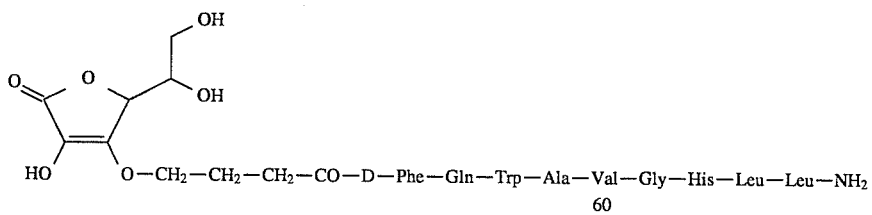

(SEQ ID NO. 116)

Other peptide derivatives of the invention can be synthesized in an analogous manner, using synthetic modifications known in the art.

Results of Assays of Test Peptides

EXAMPLE 6—

Binding Assays

In order to demonstrate the binding affinity of somatostatin (SRIF) analogs to the somatostatin receptor, the purified compounds described above were tested in somatostatin binding assays involving measurements of the in vitro inhibition of the binding of [$^{125}$I-Tyr$^{11}$]SRIF-14 to rat AR42J pancreas membranes. As indicated in Table I, purified somatostatin analogs of this invention demonstrated high binding affinities to these receptors. Additionally, the molecular weight, determined by mass spectrometry and estimated from the molecular structure, is listed in the table for each somatostatin derivative.

Similarly, the purified bombesin analog described above was tested in a bombesin binding assay. The binding assay consisted of measurements of the in vitro inhibition of the binding of [$^{125}$I-Tyr$^{11}$] bombesin to rat AR42J pancreas membranes; from the assay, the binding affinity of the bombesin analog to the GRP receptor was determined to be about 21 nM.

EXAMPLE 7—

Growth Hormone (GH) Inhibition Assay

Groups of five male Sprague Dawley rats (each having a weight between 250–300 g) were injected s.c. with a somatostatin derivative or saline. Thirty minutes prior to the selected post-drug time periods shown in table II (2 hours, 4 hours, 6 hours, 8 hours), rats were anesthetized with Nembutal i.p. (50 mg/kg). Fifteen minutes following anesthesia, an aliquot of blood was withdrawn by cardiac puncture over heparin to measure basal GH. Additionally, a s.c. injection of D-Ala$^2$-GRF (10 μg/kg) was given. Fifteen minutes later, blood was withdrawn to quantitate the stimulated GH, which was measured in plasma using a radioimmunoassay supplied by NIADDKD. The percentage of GH inhibition was calculated from differences obtained between basal and stimulated GH values.

Table II shows the effect of various purified somatostatin analogs as a function of time. The efficacy of D-Phe-c[Cys-Tyr-D-Trp-Lys-Thr-Cys]-Nal-NH$_2$ (SEQ ID NO. 113) (BIM-23060) in inhibiting growth hormone in rats is compared with other somatostatin derivatives (BIM-23167, BIM-23179, and BIM- 23181) of the invention. All derivatives demonstrate a surprising prolonged duration of action which decreases in a time-dependent fashion.

Additional experiments were conducted on D-Phe-c[Cys-Tyr-D-Trp-Lys-Abu-Cys]-Thr-NH$_2$, (SEQ ID NO. 112) a somatostatin analog, and BIM-23190, BIM-23195 and BIM-23197, to determine the ED$_{50}$ (i.e., the concentration of each compound required to inhibit fifty percent of growth hormone release after a specified time) of the respective compound. Experiments were conducted at a dose range of between 25 μg/kg and 0.25 μg/kg. Table III shows the surprising improvement of the somatostatin derivatives over the unmodified peptide at the various time intervals, indicating the time-dependent inhibition of stimulated GH release by the compounds of the invention.

EXAMPLE 8—

Antiproliferative Assay.

The purified somatostatin analogs described above were also tested for activity against rapidly proliferating cells. Table IV describes the effect of these peptides on the growth of AR42J rat pancreas tumor cells. Unlike natural somatostatin, the derivatives of the invention demonstrate substantial anti-proliferative activity. Referring now to FIG. 1, both BIM-23014C (a somatostatin analog) and BIM-23118 (a derivative of BIM-23014) inhibit the growth of AR42J rat pancreas tumor cells in a concentration-dependent fashion, with BIM-23118 being the more effective of the two compounds. Both compounds inhibit tumor cell growth to a greater extent than unmodified somatostatin analogs at equivalent concentrations.

EXAMPLE 9—

Thymidine Uptake Assay

In this assay, stock cultures of Swiss 3T3 cells are grown in Dulbecco's Modified Eagles Medium (DMEM) and supplemented with 10% fetal calf serum in a humidified atmosphere of 10% CO$_2$ and 90% air at 37° C. Cells were then seeded into 24-well cluster trays and used four days after the last change of medium. In order to arrest cells in the G1/G0 phase of the cell cycle, the a serum-free DMEM was used 24 hours prior to the thymidine uptake assay; cells were then washed twice with 1 ml aliquots of DMEM (-serum, 0.5 μM) and [methyl-$^3$H] thymidine (20 Ci/mmole, New England Nuclear). Bombesin derivatives were initially tested at 0.001, 0.01, 0.1, 1, 10, 100, 100 nM. After 28 hours at 37° C., [methyl-$^3$H] thymidine incorporation into acid-insoluble pools was assayed as follows. Cells were first washed twice with ice-cold 0.9% NaCl (1 ml aliquots) acid-soluble radioactivity was then removed by 30-minute incubation at 40° C. with 5% trichloroacetic acid (TCA). The cultures were then washed once (1 ml) with 95% ethanol and solubilized by a 30-minute incubation with 1 ml of 0.1N NaOH. The solubilized material was transferred to vials containing 10 ml ScintA (Packard), and the radioactivity determined by liquid scintillation spectrometry. This assay demonstrates the ability of the bombesin derivatives to stimulate thymidine uptake into the cells. The EC$_{50}$ was calculated to be 0.48 nm, thus demonstrating that the bombesin derivatives of the invention are potent simulators of thymidine uptake.

Methods of Use

The peptide derivatives of the invention may be administered to a mammal, particularly a human, in one of the traditional modes (e.g., orally, parenterally, transdermally, or transmucosally), in a sustained-release formulation using a biodegradable, biocompatible polymer, or by on-site delivery (e.g., in the case of an anti-cancer bombesin or somatostatin derivatives, to the lungs) using micelles, gels and liposomes. Dosages are generally the same as those currently used for therapeutic peptides in humans.

Additionally, the peptide derivatives of the invention are suitable for the improved treatment of diseases which are susceptible to treatment by the corresponding unmodified peptide. In particular, the somatostatin derivatives described above are suitable for the treatment of cancer, acromegaly, pancreatitis, trauma induced proliferation, diabetes, diabetic retinopathy, restenosis following angioplasty, AIDS, neurogenic inflammation, arteritis, and gastrointestinal problems including diarrhea.

TABLE I

IN VITRO BINDING AFFINITIES AND MOLECULAR WEIGHTS OF SOMATOSTATIN PEPTIDE DERIVATIVES

|  | MW$_{TEST}$ | MW$_{CALC}$ | IC$_{50}$ nM |
|---|---|---|---|
| SRIF-14 | — | — | 0.17 |
| SRIF-28 | — | — | 0.23 |
| BIM-23107 | 1340.4 | 1340.40 | 0.30 |
| BIM-23118 | 1313.5 | 1313.52 | 0.30 |
| BIM-23135 | 1426.2 | 1426.64 | 2.52 |
| BIM-23158 | 1299.6 | 1299.54 | 0.33 |
| BIM-23167 | 1347.6 | 1347.55 | 0.09 |
| BIM-23173 | 1235.5 | 1235.46 | 0.11 |
| BIM-23179 | 1305.9 | 1305.55 | 0.12 |
| BIM-23181 | 1435.0 | 1434.62 | 0.25 |
| BIM-23182 | 1193.8 | 1193.42 | 0.12 |
| BIM-23183 | 1323.0 | 1322.49 | 0.22 |
| BIM-23190 | 1202.8 | 1202.47 | 0.20 |
| BIM-23191 | 1314.9 | 1314.61 | 0.08 |
| BIM-23195 | 1150.8 | 1150.39 | 0.08 |
| BIM-23196 | 1243.7 | 1243.50 | 0.09 |
| BIM-23197 | 1252.7 | 1252.55 | 0.29 |
| BIM-23201 | 1262.8 | 1262.53 | 0.14 |
| BIM-23202 | 1247.0 | 1246.53 | 0.18 |

TABLE II

INHIBITION OF STIMULATED GROWTH HORMONE RELEASE IN RATS BY SOMATOSTATIN PEPTIDE DERIVATIVES

| | INHIBITION (PERCENTILE CONTROL) 25 μG/KG | | | |
|---|---|---|---|---|
|  | 2 Hours | 4 Hours | 6 Hours | 8 Hours |
| BIM-23060 | 86.39 | 64.96 | 47.62 | 38.15 |
| BIM-23167 | 92.67 | 79.54 | 59.72 | 50.14 |
| BIM-23179 | 92.79 | 63.85 | 67.78 | 68.26 |

TABLE II-continued

INHIBITION OF STIMULATED GROWTH HORMONE RELEASE IN RATS BY SOMATOSTATIN PEPTIDE DERIVATIVES

| | INHIBITION (PERCENTILE CONTROL) 25 μG/KG | | | |
|---|---|---|---|---|
| | 2 Hours | 4 Hours | 6 Hours | 8 Hours |
| BIM-23181 | 99.24 | 77.07 | 60.56 | 56.12 |

TABLE III

INHIBITION OF STIMULATED GROWTH HORMONE RELEASE IN RATS BY SOMATOSTATIN PEPTIDE DERIVATIVES ADMINISTERED S.C.

| | $ED_{50}$ (μg/kg) | | | |
|---|---|---|---|---|
| | 2 Hours | 4 Hours | 6 Hours | 8 Hours |
| BIM-23023 | 0.48 | 1.11 | 2.26 | 4.32 |
| BIM-23190 | 0.68 | 0.57 | 0.76 | 1.04 |
| BIM-23195 | 1.19 | 3.13 | 2.08 | 3.23 |
| BIM-23197 | 1.01 | 0.59 | 1.14 | 1.59 |

TABLE IV

ANTIPROLIFERATIVE ACTIVITY OF SOMATOSTATIN PEPTIDE DERIVATIVES CELL GROWTH (PERCENT OF CONTROL)[1]

| SRIF-14 | 91.3 |
|---|---|
| SRIF-28 | 98.0 |
| BIM-23014C | 74.1 |
| BIM-23107 | 67.5 |
| BIM-23109 | 72.1 |
| BIM-23118 | 61.0 |
| BIM-23135 | 62.9 |
| BIM-23167 | 60.2 |
| BIM-23173 | 67.9 |
| BIM-23181 | 69.1 |
| BIM-23182 | 68.7 |
| BIM-23183 | 69.1 |
| BIM-23195 | 69.2 |
| BIM-23197 | 66.4 |

[1]Concentration 100 nM, AR42J Rat Pancreas Tumor Cells after 8 days.

What is claimed is:

1. A peptide derivative consisting of:
a biologically active peptide moiety having a free amino group, and at least one substituent attached to said peptide moiety, wherein said substituent is selected from the group consisting of Compounds I, II, and III, wherein Compound I is:

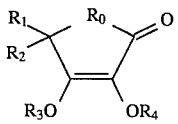

wherein:

$R_0$ is O, S, or $NR_5$, wherein $R_5$ is H or $(C_1-C_6)$ alkyl;

each $R_1$ and $R_2$, independently, is H, $(CH_2)_m OR_6$, or $CH(OR_7)CH_2OR_8$, wherein $R_6$ is H or $(C_2-C_7)$ acyl, and each $R_7$ and $R_8$, independently, is H, $(C_2-C_7)$ acyl, or $C(R_9)(R_{10})$, wherein each $R_9$ and $R_{10}$, independently, is H or $C_1-C_6$ alkyl;

or $R_1$ and $R_2$ in combination are =$CHCH_2OR_{11}$, $R_{11}$ is H or $(C_2-C_7)$ acyl, and m is an integer between 1 and 5, inclusive; and one of $R_3$ and $R_4$ is $(CH_2)_n R_{12}$ or $(CH_2)_n CH(OH)R_{12}$, wherein $R_{12}$ is CO, $CH_2$ or $SO_2$, and n is an integer between 1 and 5, inclusive;

and the other of $R_3$ and $R_4$ is H, $(C_1-C_6)$ hydroxyalkyl, or $(C_2-C_7)$ acyl; and Compound II is:

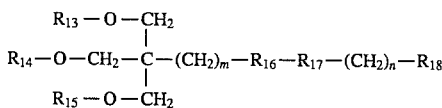

wherein:

each $R_{13}$, $R_{14}$, and $R_{15}$, independently, is H or $(C_2-C_{24})$ acyl;

$R_{16}$ is NH or absent;

$R_{17}$ is CO, O, or absent;

$R_{18}$ is CO, $CH_2$, $SO_2$, or absent;

m is an integer between 1 and 5, inclusive;

n is an integer between 1 and 5, inclusive; and

Compound III is:

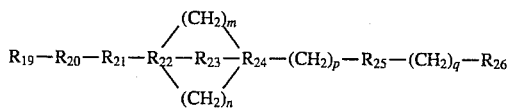

wherein:

$R_{19}$ is H, $NH_2$, an aromatic functional group, OH, $(C_1-C_6)$ hydroxyalkyl, $H(R_{27})(R_{28})$, $SO_3H$, or absent; wherein each $R_{27}$ and $R_{28}$, independently, is H or $(C_1-C_6)$ alkyl;

$R_{20}$ is O or absent;

$R_{21}$ is $(C_1-C_6)$ alkyl or absent;

$R_{22}$ is N, O, C, or CH;

$R_{23}$ is $(C_1-C_6)$ alkyl or absent;

$R_{24}$ is N, CH, or C;

$R_{25}$ is NH, O, or absent;

$R_{26}$ is $SO_2$, CO, or $CH_2$;

m is an integer between 0 and 5, inclusive;

n is an integer between 0 and 5, inclusive;

p is an integer between 0 and 5, inclusive; and q is an integer between 0 and 5, inclusive;

wherein said peptide moiety is attached to said substituent at $R_{12}$, $R_{18}$, or $R_{26}$ by a CO—N, $CH_2$—N, or $SO_2$—N bond between said substituent and said free amino group.

2. The peptide derivative of claim 1, wherein said substituent is Compound I.

3. The peptide derivative of claim 1, wherein said substituent is Compound II.

4. The peptide derivative of claim 1, wherein said substituent is Compound III.

5. The peptide derivative of claim 2, wherein $R_0$ is O, $R_1$ is $CH(OH)CH_2OH$, $R_2$ is H, and one of $R_3$ and $R_4$ is $(CH_2)_n R_{12}$ and the other of $R_3$ and $R_4$ is H or $(C_1-C_6)$ hydroxyalkyl.

6. The peptide derivative of claim 3, wherein $R_{13}$, $R_{14}$, and $R_{15}$ are H, $R_{16}$ is NH, $R_{17}$ is CO or absent, and m is 0.

7. The peptide derivative of claim 3, wherein $R_{13}$, $R_{14}$, and $R_{15}$ are H, $R_{16}$ is absent, $R_{17}$ is absent, and m is 0.

8. The peptide derivative of claim 4, wherein $R_{23}$ is $(C_1-C_6)$ alkyl, $R_{22}$ is N, C, or CH, $R_{24}$ is C, and each of m and n is an integer between 2 and 5, inclusive.

9. The peptide derivative of claim 4, wherein $R_{23}$ is absent, $R_{24}$ is N or CH, $R_{22}$ is N, O, or C, and each of m and n is an integer between 2 and 5, inclusive.

10. The peptide derivative of claim 9, wherein $R_{24}$ is N, $R_{22}$ is O, and each of $R_{19}$, $R_{20}$, and $R_{21}$ is absent.

11. The peptide derivative of claim 9, wherein each of $R_{22}$ and $R_{24}$ is N.

12. The peptide derivative of claim 11, wherein each of $R_{20}$ and $R_{25}$ is absent.

13. The peptide derivative of claim 12, wherein $R_{19}$ is OH, $R_{21}$ is $(C_1-C_6)$ alkyl, and p is 0.

14. The peptide derivative of claim 5, wherein said peptide moiety is selected from the group consisting of: somatostatin, bombesin, calcitonin, calcitonin gene related peptide, amylin, parathyroid hormone, gastrin releasing peptide, melanocyte stimulating hormone, adrenocorticotrophic hormone, parathyroid related peptide, luteinizing hormone-releasing hormone, growth hormone releasing factor, growth hormone releasing peptide, cholecystokinin, glucagon, bradykinin, glucagon-like peptide, gastrin enkephalin, neuromedins, endothelin, substance P, neuropeptide Y, peptide YY, vasoactive intestinal peptide, guanylin, pituitary adenylate cyclase activating polypeptide, beta-cell tropin, adrenomedullin, and a derivative, a fragment, or an analog thereof.

15. The peptide derivative of claim 14, wherein said peptide moiety is somatostatin or a derivative, a fragment, or an analog thereof.

16. The peptide derivative of claim 6, wherein said peptide moiety is selected from the group consisting of: somatostatin, bombesin, calcitonin, calcitonin gene related peptide, amylin, parathyroid hormone, gastrin releasing peptide, melanocyte stimulating hormone, adrenocorticotrophic hormone, parathyroid related peptide, luteinizing hormone-releasing hormone, growth hormone releasing factor, growth hormone releasing peptide, cholecystokinin, glucagon, bradykinin, glucagon-like peptide, gastrin enkephalin, neuromedins, endothelin, substance P, neuropeptide Y, peptide YY, vasoactive intestinal peptide, guanylin, pituitary adenylate cyclase activating polypeptide, beta-cell tropin, adrenomedullin, and a derivative, a fragment, and an analog thereof.

17. The peptide derivative of claim 16, wherein said peptide moiety is somatostatin or a derivative, a fragment, or an analog thereof.

18. The peptide derivative of claim 7, wherein said peptide moiety is selected from the group consisting of: somatostatin, bombesin, calcitonin, calcitonin gene related peptide, amylin, parathyroid hormone, gastrin releasing peptide, melanocyte stimulating hormone, adrenocorticotrophic hormone, parathyroid related peptide, luteinizing hormone-releasing hormone, growth hormone releasing factor, growth hormone releasing peptide, cholecystokinin, glucagon, Bradykinin, glucagon-like peptide, gastrin enkephalin, neuromedins, endothelin, substance P, neuropeptide Y, peptide YY, vasoactive intestinal peptide, guanylin, pituitary adenylate cyclase activating polypeptide, beta-cell tropin, adrenomedullin, and a derivative, a fragment, or an analog thereof.

19. The peptide derivative of claim 18, wherein said peptide moiety is somatostatin or a derivative, a fragment, or an analog thereof.

20. The peptide derivative of claim 13, wherein said peptide moiety is selected from the group consisting of: somatostatin, bombesin, calcitonin, calcitonin gene related peptide, amylin, parathyroid hormone, gastrin releasing peptide, melanocyte stimulating hormone, adrenocorticotrophic hormone, parathyroid related peptide, luteinizing hormone-releasing hormone, growth hormone releasing factor, growth hormone releasing peptide, cholecystokinin, glucagon, Bradykinin, glucagon-like peptide, gastrin enkephalin, neuromedins, endothelin, substance P, neuropeptide Y, peptide YY, vasoactive intestinal peptide, guanylin, pituitary adenylate cyclase activating polypeptide, beta-cell tropin, adrenomedullin, and a derivative, a fragment, or an analog thereof.

21. The peptide derivative of claim 20, wherein said peptide moiety is somatostatin or a derivative, a fragment, or an analog thereof.

22. The peptide derivative of claim 21, wherein said somatostatin analog is: H-D-Phe-c[Cys-Try-D-Trp-Lys-Abu-Cys]-Thr-NH$_2$, H-D-Phe-c[Cys-Tyr-D-Trp-Lys-Thr-Cys]-Nal-NH$_2$, or H-D-Nal-c[Cys-Tyr-D-Trp-Lys-Val-Cys]-Thr-NH$_2$.

23. The peptide derivative of claim 14, wherein said substituent is one of:

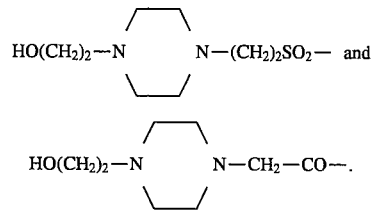

24. The peptide derivative of claim 1, wherein said peptide moiety is selected from the group consisting of: somatostatin, bombesin, calcitonin, calcitonin gene related peptide (CGRP), amylin, parathyroid hormone (PTH), gastrin releasing peptide (GRP), melanocyte stimulating hormone (MSH), adrenocorticotrophic hormone (ACTH), parathyroid related peptide (PTHrP), luteinizing hormone-releasing hormone (LHRH), growth hormone releasing factor (GHRF), growth hormone releasing peptide (GHRP), cholecystokinin (CCK), glucagon, Bradykinin, glucagon-like peptide (GLP), gastrin, enkephalin, neuromedins, endothelin, substance P, neuropeptide Y (NPY), peptide YY (PYY), vasoactive intestinal peptide (VIP), guanylin, pituitary adenylate cyclase activating polypeptide (PACAP), beta-cell tropin, adrenomedulin, and derivatives, fragments, and analogs thereof.

25. The peptide derivative of claim 24, wherein said peptide moiety is somatostatin or a derivative, fragment, or analog thereof.

26. The peptide derivative of claim 25, wherein said somatostatin analog is one of: H-D-Phe-c[Cys-Tyr-D-Trp-Lys-Abu-Cys]-Thr-NH$_2$, (SEQ ID NO. 112); H-D-Phe-c[Cys-Tyr-D-Trp-Lys-Thr-Cys]-Nal-NH$_2$, (SEQ ID NO. 113); and H-D-Nal-c[Cys-Tyr-D-Trp-Lys-Val-Cys]-Thr-NH$_2$ (SEQ ID NO. 112).

27. The peptide derivative of claim 24, wherein said peptide moiety is bombesin or a derivative, fragment or analog thereof.

28. The peptide derivative of claim 1, wherein said peptide derivative is one of:

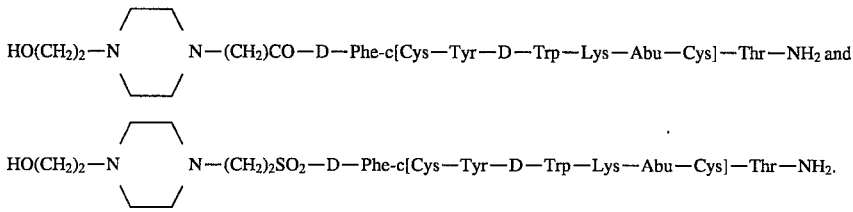

(SEQ ID NO. 112)

UNITED STATES PATENT AND TRADEMARK OFFICE
CERTIFICATE OF CORRECTION

PATENT NO. : 5,552,520

DATED : September 3, 1996

INVENTOR(S) : Sun H. Kim, Susan R. Keyes, Sylviane Moreau, Zheng X. Dong, John Taylor It is certified that error appears in the above-identified patent and that said Letters Patent is hereby corrected as shown below:

Col. 3, line 26, replace "$NH_{-2}$" with --$NH_2$--.

Col. 3, line 26, replace "(SEQ. ID NO. 1)" with --(SEQ. ID NO. 2)--.

Col. 3, line 40, replace "(SEQ. ID NO. 2)" with --(SEQ. ID NO. 1)--.

Col. 6, line 56, insert --(SEQ. ID NO. 31)-- after "NHEt".

Col. 7, line 21, insert -- (SEQ. ID NO. 47) -- after "$NH_2$".

Col. 7, line 62, insert --(SEQ.ID NO. 67)-- after "Phe); "

Col. 7, line 35, replace "No. 53" with --No. 52--.

Col. 7, line 37, replace "No. 54" with --No. 53--.

Col. 7, line 39, replace "No. 55" with --No. 54--.

Col. 7, line 43, replace "No. 56" with --No. 55--.

Col. 7, line 45, replace "No. 57" with --No. 56--.

UNITED STATES PATENT AND TRADEMARK OFFICE
CERTIFICATE OF CORRECTION

PATENT NO. : 5,552,520

DATED : September 3, 1996

INVENTOR(S) : Sun H. Kim, Susan R. Keyes, Sylviane Moreau, Zheng X. Dong, John Taylor It is certified that error appears in the above-identified patent and that said Letters Patent is hereby corrected as shown below:

Col. 7, line 47, replace "No. 58" with --No. 57--.

Col. 7, line 48, replace "No. 59" with --No. 58--.

Col. 7, line 50, replace "No. 60" with --No. 59--.

Col. 7, line 51, replace "No. 61" with --No. 60--.

Col. 7, line 52, replace "No. 62" with --No. 61--.

Col. 7, line 53, replace "No. 63" with --No. 62--.

Col. 7, line 55, replace "No. 64" with --No. 63--.

Col. 7, line 57, replace "No. 65" with --No. 64--.

Col. 7, line 59, replace "No. 66" with --No. 65--.

Col. 7, line 61, replace "No. 67" with --No. 66--.

Col. 8, line 60, replace "95" with --93--.

Col. 10, line 46, replace "108" with --107--.

Col. 18, line 31, replace "14.3" with --4.3--.

Col. 37, SEQ. ID NO. 29, (D) OTHER INFORMATION, replace "($CH_2$, hexyl)" with --($CH_3$, hexyl)--.

UNITED STATES PATENT AND TRADEMARK OFFICE
CERTIFICATE OF CORRECTION

PATENT NO.  : 5,552,520

DATED       : September 3, 1996

INVENTOR(S) : Sun H. Kim, Susan R. Keyes, Sylviane Moreau, Zheng X. Dong, John Taylor It is certified that error appears in the above-identified patent and that said Letters Patent is hereby corrected as shown below:

Col. 51, SEQ. ID NO: 55, (D) OTHER INFORMATION, replace "Phenylalanine" with --Tryptophan--, and replace "Tryptophan" with --N-Me-Lysine-- (F&R error).

Col 57, SEQ ID NO: 67, (D) OTHER INFORMATION, replace "Xaa at position 3 is D-Tryptophan" with --Xaa at position 3 is D-Threonine-- (F&R error).

Col. 83, line 53, replace "1" with --0--.

Col. 84, line 16, replace "0" with --2--.

Col. 84, line 17, replace "0" with --2--.

Col. 86, line 43, replace "112" with --110--.

Signed and Sealed this

Seventh Day of October, 1997

*Attest:*

BRUCE LEHMAN

*Attesting Officer*  Commissioner of Patents and Trademarks